(12) United States Patent
Bowen, III et al.

(10) Patent No.: US 7,022,803 B2
(45) Date of Patent: Apr. 4, 2006

(54) MODIFIED SILANE COMPOUNDS

(75) Inventors: Daniel Edward Bowen, III, Munroe Falls, OH (US); Eric Sean Castner, Uniontown, OH (US)

(73) Assignee: The Goodyear Tire & Rubber Company, Akron, OH (US)

( * ) Notice: Subject to any disclaimer, the term of this patent is extended or adjusted under 35 U.S.C. 154(b) by 357 days.

(21) Appl. No.: 10/696,358

(22) Filed: Oct. 29, 2003

(65) Prior Publication Data

US 2005/0075447 A1    Apr. 7, 2005

Related U.S. Application Data

(62) Division of application No. 10/222,739, filed on Aug. 16, 2002.

(60) Provisional application No. 60/312,851, filed on Aug. 16, 2001, provisional application No. 60/326,042, filed on Sep. 28, 2001.

(51) Int. Cl.
*C08G 77/20* (2006.01)

(52) U.S. Cl. .................... 528/32; 526/307.5; 526/279; 528/40

(58) Field of Classification Search ............... 526/279, 526/307.5; 528/32, 40
See application file for complete search history.

(56) References Cited

U.S. PATENT DOCUMENTS

| | | | |
|---|---|---|---|
| 3,287,291 A | * | 11/1966 | Ender .......................... 528/18 |
| 4,474,926 A | | 10/1984 | Burroway ................... 524/710 |
| 4,968,741 A | | 11/1990 | Burroway et al. .......... 524/710 |
| 5,973,067 A | * | 10/1999 | Nakamura et al. .......... 524/858 |

* cited by examiner

*Primary Examiner*—Ling-Sui Choi
(74) *Attorney, Agent, or Firm*—Alvin T. Rockhill

(57) ABSTRACT

This invention relates to the reversible protection of hydroxy-silane functional groups by acid cleavable protecting groups. The development of reversible protecting groups greatly enhances the current utility of silanes while introducing further novel applications. For instance, reversibly protected silanes are of particular value in applications where room temperature cure and/or adhesion is of value, such as coatings, high resolution imaging, caulks, adhesives, sealants, gaskets, and silicones. Reversibly protected silanes can also be beneficially used in reticulating agents, and in sizing agents, tires, and release coatings. The incorporation of reversibly protected silanes into coating resins is of particular value. The reversibly protected silane can be incorporated into the coating resin by polymerizing a monomer containing the reversibly protected silane into the resin or by post-addition into the coating formulation. The reversibly protected silane remains protected under basic conditions, such as in a coating formulation that contains a volatile base, for instance ammonium hydroxide. However, deprotection occurs under mildly acidic conditions. Thus, as a coating formulation containing a volatile base dries the volatile base evaporates and deprotection occurs. This allows for controlled room temperature crosslinking to occur with hydroxy-functionalized polymers. The present invention more specifically discloses a modified silane compound consisting of a silane having 3 or 4 acetal moieties bonded thereto.

20 Claims, No Drawings

MODIFIED SILANE COMPOUNDS

This is a divisional of U.S. patent application Ser. No. 10/222,739, filed on Aug. 16, 2002, which claims the benefit of U.S. Provisional Application Ser. No. 60/312,851, filed on Aug. 16, 2001, and U.S. Provisional Application Ser. No. 60/326,042, filed on Sep. 28, 2001.

BACKGROUND OF THE INVENTION

Most conventional coating resins are insoluble in water. Therefore, in general practice, they have been dissolved in a suitable organic solvent or dispersed in water with the aid of an emulsifying agent or surfactant in order to provide a coating composition suitable for application to a substrate surface. A serious disadvantage of organic solvent solutions is that they are potentially toxic, flammable and environmental pollutants. Water-reducible coatings greatly reduce the magnitude of these problems. For this reason, water-based paints are currently being used as a replacement for oil-based paints in many applications.

Various water-reducible coating resins, such as the one described in U.S. Pat. No. 4,474,926, have been developed. Water-reducible coatings that utilize such resins have been developed for a variety of purposes and have been widely accepted in many applications such as highway striping paint.

U.S. Pat. No. 4,968,741 describes a coating for metal substrates which provides improved corrosion and rust resistance. Such coatings are of the water-reducible type and can be beneficially utilized in the automotive industry and other applications where good rust resistance is needed. For instance, such coatings are excellent for coating bridges and other outdoor metal structures.

It is also critical for coatings made with water-reducible coating formulations to offer the desired combination of physical and chemical properties. For instance, in many applications, it is important for the coating to exhibit excellent flexibility, excellent ultra-violet light resistance and excellent solvent resistance. In applications which involve metal substrates, outstanding corrosion and rust-resistance is normally also sought.

For purposes of this patent application, an aqueous coating system is considered to be a colloidal dispersion of a resin in water which can be reduced by the addition of water and which forms a durable coating when applied to a substrate surface. The term aqueous coating system is used herein interchangeably with the term water-reducible coating. Other names which are sometimes applied to water-reducible coatings are water-born, water-solubilized and water-dilutable.

SUMMARY OF THE INVENTION

This invention relates to the reversible protection of hydroxy-silane functional groups by acid cleavable protecting groups. The development of reversible protecting groups greatly enhances the current utility of silanes while introducing further novel applications. For instance, reversibly protected silanes are of particular value in applications where room temperature cure and/or adhesion is of value, such as high resolution imaging, caulks, adhesives, sealents, gaskets, and silicones. Reversibly protected silanes can also be beneficially used in reticulating agents, and in sizing agents, tires, and release coatings.

The incorporation of reversibly protected silanes into coating resins is of particular value. The reversibly protected silane can be incorporated into the coating resin by polymerizing a monomer containing the reversibly protected silane into the resin or by post-addition into the coating formulation. The reversibly protected silane remains protected under basic conditions, such as in a coating formulation that contains a volatile base, for instance ammonium hydroxide. However, deprotection occurs under mildly acidic conditions. Thus, as a coating formulation containing a volatile base dries the volatile base evaporates and deprotection occurs. This allows for controlled room temperature crosslinking to occur with hydroxy-functionalized polymers. Chemical adhesion to hydroxy-group containing substrates, such as metal, glass, and wood, also occurs. This makes coating resins that contain reversibly protected silanes especially valuable for coating metals, glass, and wood. Since such coating formulations that contain reversibly protected silanes are curable at room temperature they are much easier to apply and cure than conventional systems. Benefits associated with using coating formulations that contain reversibly protected silanes are realized in a wide variety of applications including structural coatings, anti-corrosion coatings, and marine biofouling coatings.

This invention further relates to the synthesis of a latex which can be used in making self-crosslinking water-reducible coating compositions, such as paints, which offer excellent solvent resistance, reduced drying time and improved adhesion to metal and glass. Coatings which are formulated with the latex of this invention are environmentally advantageous because they contain no or extremely low levels of volatile organic compounds and additionally offer excellent flexibility and excellent ultra-violet light resistance.

The present invention more specifically discloses a water-reducible coating composition which is comprised of (1) water; (2) a resin having repeat units which are derived from (a) about 30 to about 75 weight percent vinyl aromatic monomers, (b) about 20 to about 65 weight percent of alkyl acrylate monomers, (c) about 1 to about 8 weight percent alkyl propenoic acid monomers and (d) about 0.5 to about 5 weight percent reversibly protected silane monomers, based on 100 weight percent monomers; (3) a wetting agent; and (4) a defoamer.

The subject invention further reveals a process for producing a neutralized latex that is useful in the manufacture of self-crosslinkable water-reducible coatings which comprises: (1) free radical aqueous emulsion polymerizing at a pH of less than about 3.5, a monomer mixture which comprises, based on 100 weight percent monomers: (a) from about 30 to about 75 weight percent vinyl aromatic monomers, (b) from about 20 to about 65 weight percent of alkyl acrylate monomers, (c) from about 1 to about 8 weight percent alkyl propenoic acid monomers and (d) about 0.5 to about 5 weight percent reversibly protected silane monomers; in the presence of about 0.2 to 3 phm of at least one α-olefin sulfonate soap to produce a latex; and (2) neutralizing the latex with ammonia to a pH which is within the range of about 7 to about 10.5 to produce the neutralized latex.

The present invention also discloses a latex which is useful in the manufacture of self-crosslinkable water-reducible coatings, said latex being comprised of (1) water, (2) an emulsifier and (3) a polymer which is comprised of repeat units which are derived from (a) about 30 to about 75 weight percent vinyl aromatic monomers, (b) about 20 to about 65 weight percent of alkyl acrylate monomers, (c) about 1 to about 8 weight percent alkyl propenoic acid monomers and (d) about 0.5 to about 5 weight percent reversibly protected silane monomers.

The present invention further discloses a modified silane compound consisting of a silane having 3 or 4 acetal moieties bonded thereto.

The present invention further discloses a modified silane compound consisting of silane having 2 acetal moieties bonded thereto with the proviso that the silane compound does not contain a methyl, ethyl, or phenyl group if the silane compound has the following structure:

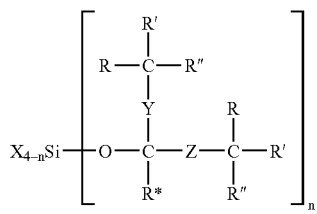

wherein n represents an integer.

The present invention further discloses a modified silane compound having a structural formula selected from the group consisting of:

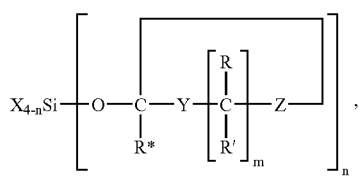

(1)

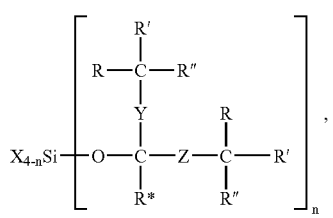

(2)

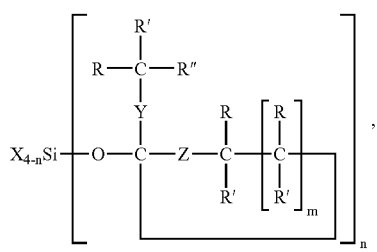

(3)

and

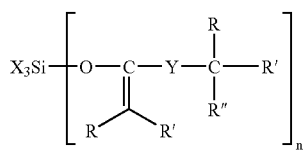

(4)

wherein n represents an integer from 2 to 4; wherein m represents an integer from 1 to about 20; with the proviso that m can represent the integer 0 for structures of formula (3) wherein Z represents the group C(R)R'; wherein X groups can be the same or different; wherein X represents a chemical moiety; with the proviso that X does not represent a methyl group, an ethyl group, or a phenyl group in cases where the modified silane compound is of structural formula (2) wherein n represents the integer 1 or the integer 2 wherein R* represents a hydrogen atom wherein Y represents an oxygen atom wherein Z represents the moiety C(R)R'; wherein R, R', and R" can be the same or different and are selected from the group consisting of hydrogen atoms, alkyl groups containing from 1 to about 12 carbon atoms, aryl groups containing from about 6 to about 18 carbon atoms, alkaryl groups containing from 7 to about 18 carbon atoms, alkoxy groups containing from 1 to about 18 carbon atoms, hydroxy groups, and halide atoms; wherein R* is selected from the group consisting of hydrogen atoms, alkyl groups containing from 1 to about 12 carbon atoms, aryl groups containing from about 6 to about 18 carbon atoms, and alkaryl groups containing from 7 to about 18 carbon atoms; wherein R, R', R", and R* can be bonded together in any combination in cases where R, R', R", and R* are not hydrogen atoms, halide atoms, or hydroxy groups; wherein Y represents a moiety selected from the group consisting of C(R)R', oxygen, sulfur, nitrogen, and phosphorus; wherein Z represents a moiety selected from the group consisting of C(R)R', oxygen, sulfur, nitrogen, and phosphorus; with the proviso that Y and Z can not both represent the moiety C(R)R'; wherein the contiguous cyclic ring in formulas (1) and (3) can contain heteroatoms selected from the group consisting of oxygen, sulfur, nitrogen, phosphorus, and silicon in cases where m represents an integer greater than 1; wherein the contiguous cyclic ring in formulas (1) and (3) can be saturated or unsaturated in cases where m represents an integer greater than 1; wherein said alkyl groups, aryl groups, alkaryl groups, and alkoxy groups can contain halide atoms and heteroatoms selected from the group consisting of oxygen, sulfur, nitrogen, phosphorus, and silicon.

The present invention further discloses a modified silane compound having a structural formula selected from the group consisting of:

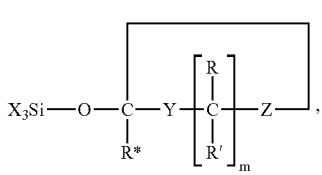

(1)

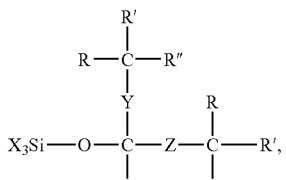

(2)

and

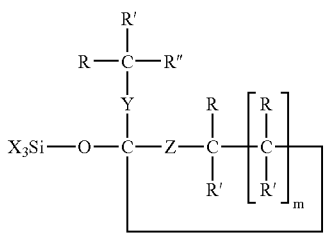

(3)

wherein m represents an integer from 1 to about 20; with the proviso that m can represent the integer 0 for structures of formula (3) wherein Z represents the group C(R)R' wherein X represents a chemical moiety other than a methyl group; wherein X groups can be the same or different; wherein X represents a chemical moiety other than a methyl, ethyl, butyl, or phenyl in cases where the modified silane compound is of structural formula (1) wherein Y represents an oxygen atom wherein Z represents the moiety C(R)R' wherein m in equal to the integer 2 or the integer 3; wherein X represents a chemical moiety other than a methyl group, a tertiary butyl group, or a phenyl group in cases where the modified silane compound is of structural formula (3) wherein Y represents an oxygen atom wherein Z represents the moiety C(R)R' wherein m in equal to the integer 3; wherein R, R', and R" can be the same or different and are selected from the group consisting of hydrogen atoms, alkyl groups containing from 1 to about 12 carbon atoms, aryl groups containing from about 6 to about 18 carbon atoms, alkaryl groups containing from 7 to about 18 carbon atoms, alkoxy groups containing from 1 to about 18 carbon atoms, hydroxy groups, and halide atoms; wherein R* is selected from the group consisting of hydrogen atoms, alkyl groups containing from 1 to about 12 carbon atoms, aryl groups containing from about 6 to about 18 carbon atoms, and alkaryl groups containing from 7 to about 18 carbon atoms; wherein R, R', R", and R* can be bonded together in any combination in cases where R, R', R", and R* are not hydrogen atoms, halide atoms, or hydroxy groups; wherein Y represents a moiety selected from the group consisting of C(R)R', oxygen, sulfur, nitrogen, and phosphorus; wherein Z represents a moiety selected from the group consisting of C(R)R', oxygen, sulfur, nitrogen, and phosphorus; with the proviso that Y and Z can not both represent the moiety C(R)R'; wherein the contiguous cyclic ring in formulas (1) and (3) may contain heteroatoms selected from the group consisting of oxygen, sulfur, nitrogen, phosphorus, and silicon in cases where m represents an integer greater than 1; wherein the contiguous cyclic ring in formulas (1) and (3) may be saturated or unsaturated in cases where m represents an integer greater than 1; wherein said alkyl groups, aryl groups, alkaryl groups, and alkoxy groups can contain halide atoms and heteroatoms selected from the group consisting of oxygen, sulfur, nitrogen, phosphorus, and silicon.

The present invention further discloses a monomer having a structural formula selected from the group consisting of:

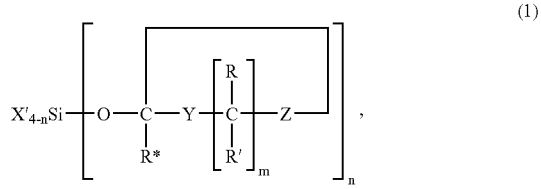

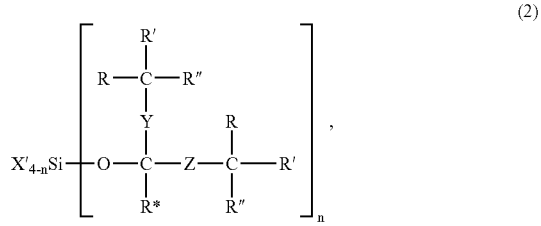

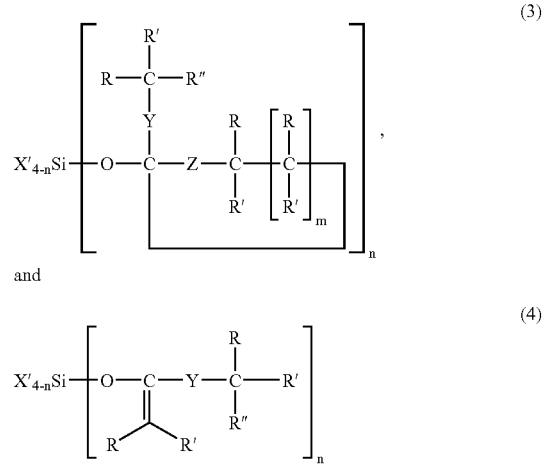

wherein n represents an integer from 1 to 3; wherein m represents an integer from 1 to about 20; with the proviso that m can represent the integer 0 for structures of formula (3) wherein Z represents the group C(R)R'; wherein X' groups can be the same or different; wherein X' represents an unsaturated moiety containing at least one non-aromatic double bond; wherein R, R', and R" can be the same or different and are selected from the group consisting of hydrogen atoms, alkyl groups containing from 1 to about 12 carbon atoms, aryl groups containing from about 6 to about 18 carbon atoms, alkaryl groups containing from 7 to about 18 carbon atoms, alkoxy groups containing from 1 to about 18 carbon atoms, hydroxy groups, and halide atoms; wherein R* is selected from the group consisting of hydrogen atoms, alkyl groups containing from 1 to about 12 carbon atoms, aryl groups containing from about 6 to about 18 carbon atoms, and alkaryl groups containing from 7 to about 18 carbon atoms; wherein R, R', R", and R* can be bonded together in any combination in cases where R, R', R", and R* are not hydrogen atoms, halide atoms, or hydroxy groups; wherein Y represents a moiety selected from the group consisting of C(R)R', oxygen, sulfur, nitrogen, and phosphorus; wherein Z represents a moiety selected from the group consisting of C(R)R', oxygen, sulfur, nitrogen, and phosphorus; with the proviso that Y and Z can not both represent the moiety C(R)R'; wherein the contiguous cyclic ring in formulas (1) and (3) can contain heteroatoms selected from the group consisting of oxygen, sulfur, nitrogen, phosphorus, and silicon in cases where m represents an integer greater than 1; wherein the contiguous cyclic ring in formulas (1) and (3) can be saturated or unsaturated in cases where m represents an integer greater than 1; wherein said alkyl groups, aryl groups, alkaryl groups, and alkoxy groups can contain halide atoms and heteroatoms selected from the group consisting of oxygen, sulfur, nitrogen, phosphorus, and silicon.

The present invention further discloses a polymer which is comprised of polymer chains having at least one modified silane moiety bonded thereto, wherein said modified silane moiety is of a structural formula selected from the group consisting of:

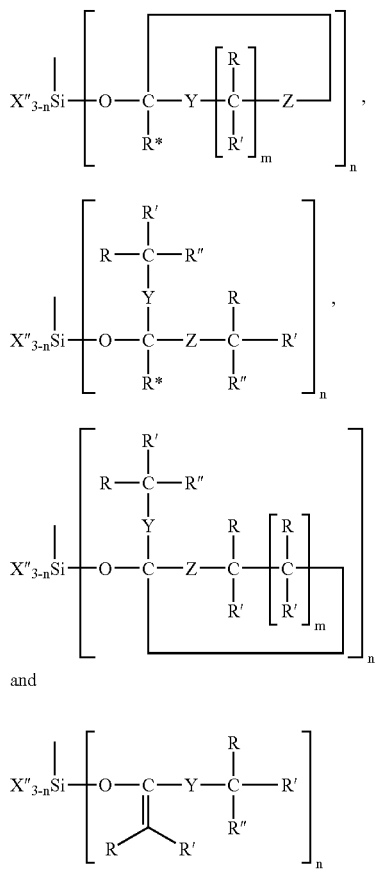

wherein n represents an integer from 1 to 3; wherein m represents an integer from 1 to about 20; with the proviso that m can represent the integer 0 for structures of formula (3) wherein Z represents the group C(R)R'; wherein X" groups can be the same or different; wherein X" represents a chemical moiety; wherein R, R', and R" can be the same or different and are selected from the group consisting of hydrogen atoms, alkyl groups containing from 1 to about 12 carbon atoms, aryl groups containing from about 6 to about 18 carbon atoms, alkaryl groups containing from 7 to about 18 carbon atoms, alkoxy groups containing from 1 to about 18 carbon atoms, hydroxy groups, and halide atoms; wherein R* is selected from the group consisting of hydrogen atoms, alkyl groups containing from 1 to about 12 carbon atoms, aryl groups containing from about 6 to about 18 carbon atoms, and alkaryl groups containing from 7 to about 18 carbon atoms; wherein R, R', R", and R* can be bonded together in any combination in cases where R, R', R", and R* are not hydrogen atoms, halide atoms, or hydroxy groups; wherein Y represents a moiety selected from the group consisting of C(R)R', oxygen, sulfur, nitrogen, and phosphorus; wherein Z represents a moiety selected from the group consisting of C(R)R', oxygen, sulfur, nitrogen, and phosphorus; with the proviso that Y and Z can not both represent the moiety C(R)R'; wherein the contiguous cyclic ring in formulas (1) and (3) can contain heteroatoms selected from the group consisting of oxygen, sulfur, nitrogen, phosphorus, and silicon in cases where m represents an integer greater than 1; wherein the contiguous cyclic ring in formulas (1) and (3) can be saturated or unsaturated in cases where m represents an integer greater than 1; wherein said alkyl groups, aryl groups, alkaryl groups, and alkoxy groups can contain halide atoms and heteroatoms selected from the group consisting of oxygen, sulfur, nitrogen, phosphorus, and silicon.

The present invention further discloses a modified silane compound having a structural formula selected from the group consisting of:

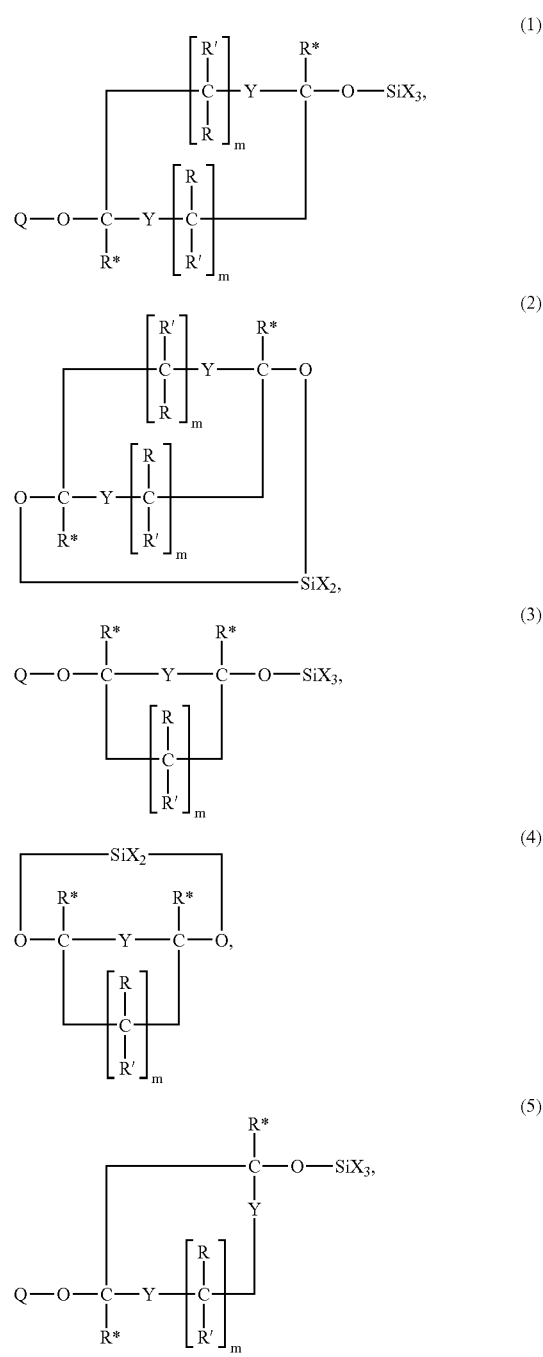

-continued

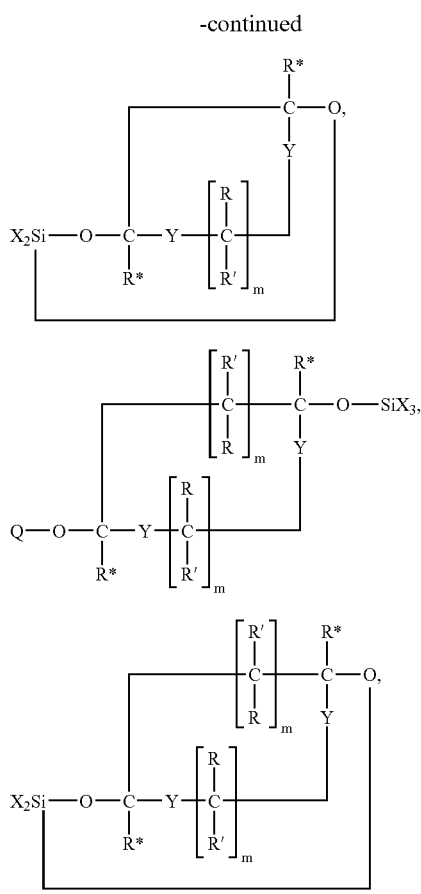

wherein m represents an integer from 1 to about 20; wherein X groups can be the same or different; wherein X represents a chemical moiety; wherein Q is selected from the group consisting of hydrogen atoms and $SiX_3$; wherein R and R' can be the same or different and are selected from the group consisting of hydrogen atoms, alkyl groups containing from 1 to about 12 carbon atoms, aryl groups containing from about 6 to about 18 carbon atoms, alkaryl groups containing from 7 to about 18 carbon atoms, alkoxy groups containing from 1 to about 18 carbon atoms, hydroxy groups, and halide atoms; wherein R* is selected from the group consisting of hydrogen atoms, alkyl groups containing from 1 to about 12 carbon atoms, aryl groups containing from about 6 to about 18 carbon atoms, and alkaryl groups containing from 7 to about 18 carbon atoms; wherein R, R', and R* can be bonded together in any combination in cases where R, R', and R* are not hydrogen atoms, halide atoms, or hydroxy groups; wherein Y represents a moiety selected from the group consisting of oxygen, sulfur, nitrogen, and phosphorus; wherein Z represents a moiety selected from the group consisting of C(R)R', oxygen, sulfur, nitrogen, and phosphorus; wherein the contiguous cyclic ring in formulas (1), (2), (3), (4), (5), (6), (7), (8), (9), and (10) can contain heteroatoms selected from the group consisting of oxygen, sulfur, nitrogen, phosphorus, and silicon in cases where m represents an integer greater than 1; wherein the contiguous cyclic ring in formulas (1), (2), (3), (4), (5), (6), (7), (8), (9), and (10) can be saturated or unsaturated in cases where m represents an integer greater than 1; wherein said alkyl groups, aryl groups, alkaryl groups, and alkoxy groups can contain halide atoms and heteroatoms selected from the group consisting of oxygen, sulfur, nitrogen, phosphorus, and silicon.

The present invention further discloses a monomer having a structural formula selected from the group consisting of:

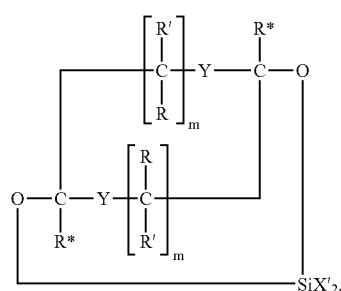

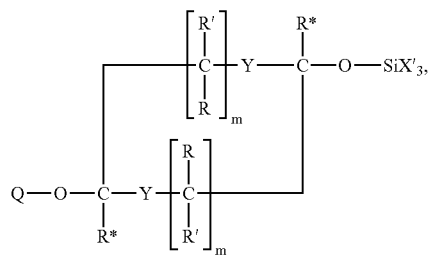

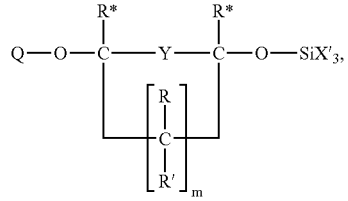

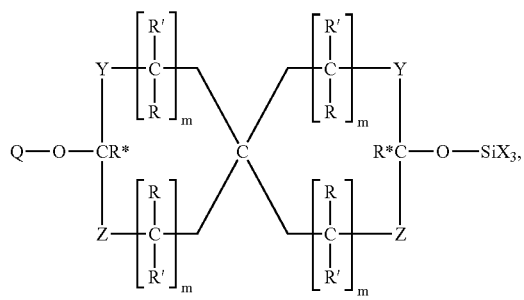

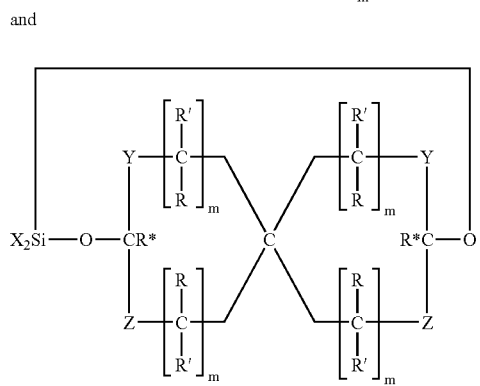

-continued

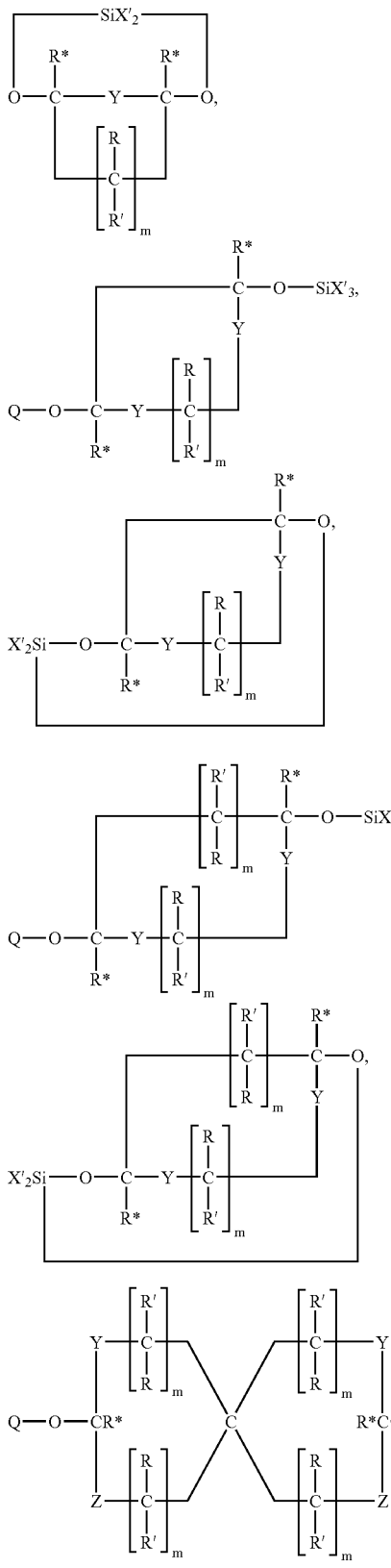

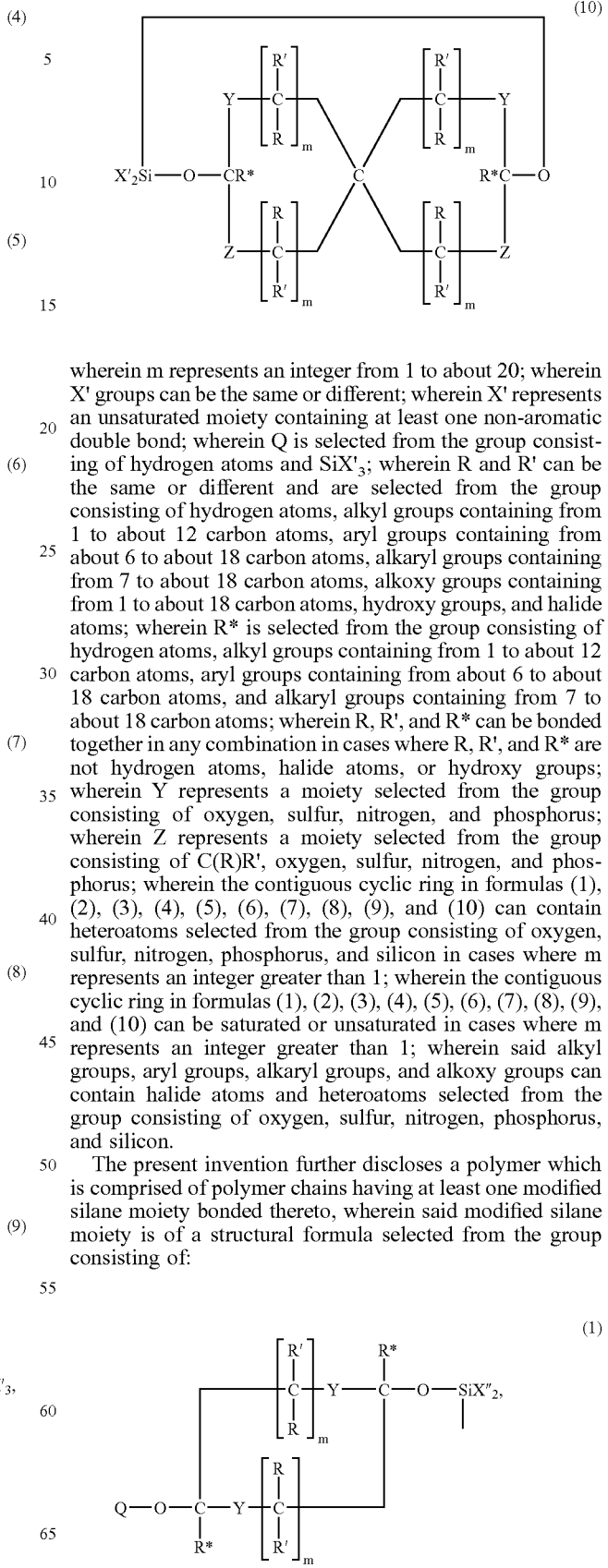

wherein m represents an integer from 1 to about 20; wherein X' groups can be the same or different; wherein X' represents an unsaturated moiety containing at least one non-aromatic double bond; wherein Q is selected from the group consisting of hydrogen atoms and $SiX'_3$; wherein R and R' can be the same or different and are selected from the group consisting of hydrogen atoms, alkyl groups containing from 1 to about 12 carbon atoms, aryl groups containing from about 6 to about 18 carbon atoms, alkaryl groups containing from 7 to about 18 carbon atoms, alkoxy groups containing from 1 to about 18 carbon atoms, hydroxy groups, and halide atoms; wherein R* is selected from the group consisting of hydrogen atoms, alkyl groups containing from 1 to about 12 carbon atoms, aryl groups containing from about 6 to about 18 carbon atoms, and alkaryl groups containing from 7 to about 18 carbon atoms; wherein R, R', and R* can be bonded together in any combination in cases where R, R', and R* are not hydrogen atoms, halide atoms, or hydroxy groups; wherein Y represents a moiety selected from the group consisting of oxygen, sulfur, nitrogen, and phosphorus; wherein Z represents a moiety selected from the group consisting of C(R)R', oxygen, sulfur, nitrogen, and phosphorus; wherein the contiguous cyclic ring in formulas (1), (2), (3), (4), (5), (6), (7), (8), (9), and (10) can contain heteroatoms selected from the group consisting of oxygen, sulfur, nitrogen, phosphorus, and silicon in cases where m represents an integer greater than 1; wherein the contiguous cyclic ring in formulas (1), (2), (3), (4), (5), (6), (7), (8), (9), and (10) can be saturated or unsaturated in cases where m represents an integer greater than 1; wherein said alkyl groups, aryl groups, alkaryl groups, and alkoxy groups can contain halide atoms and heteroatoms selected from the group consisting of oxygen, sulfur, nitrogen, phosphorus, and silicon.

The present invention further discloses a polymer which is comprised of polymer chains having at least one modified silane moiety bonded thereto, wherein said modified silane moiety is of a structural formula selected from the group consisting of:

-continued

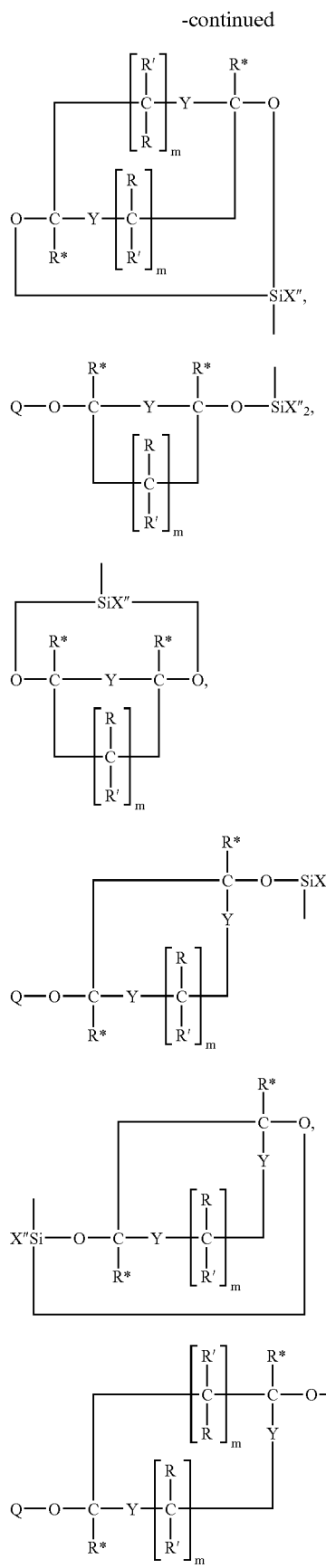

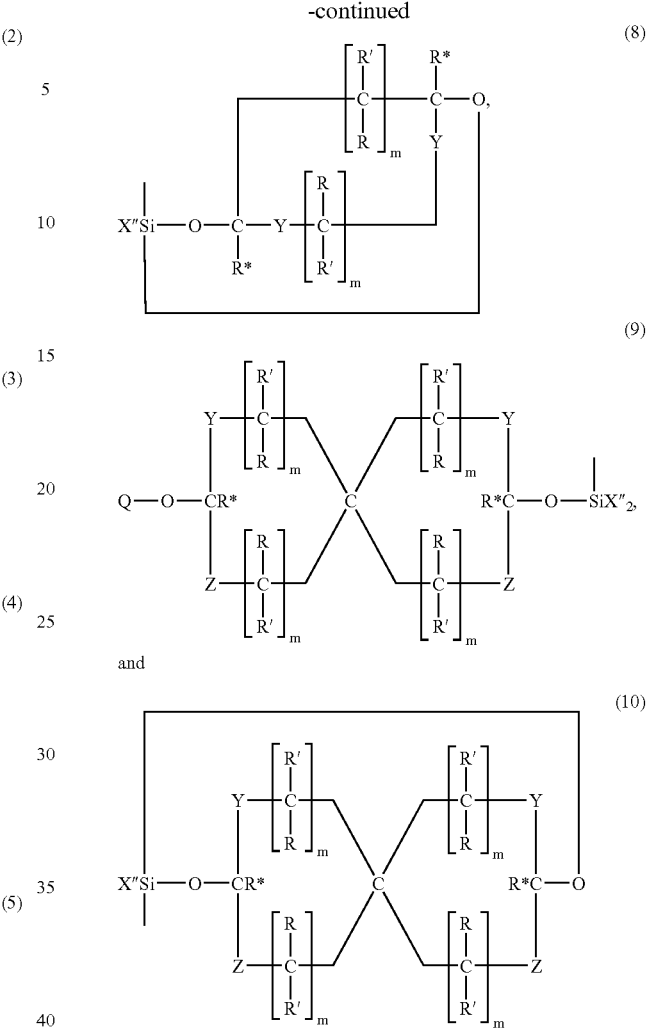

wherein m represents an integer from 1 to about 20; wherein X" groups can be the same or different; wherein X" represents a chemical moiety; wherein Q is selected from the group consisting of hydrogen atoms and X"$_2$Si—; wherein R and R' can be the same or different and are selected from the group consisting of hydrogen atoms, alkyl groups containing from 1 to about 12 carbon atoms, aryl groups containing from about 6 to about 18 carbon atoms, alkaryl groups containing from 7 to about 18 carbon atoms, alkoxy groups containing from 1 to about 18 carbon atoms, hydroxy groups, and halide atoms; wherein R* is selected from the group consisting of hydrogen atoms, alkyl groups containing from 1 to about 12 carbon atoms, aryl groups containing from about 6 to about 18 carbon atoms, and alkaryl groups containing from 7 to about 18 carbon atoms; wherein R, R', and R* can be bonded together in any combination in cases where R, R', R", and R* are not hydrogen atoms, halide atoms, or hydroxy groups; wherein Y represents a moiety selected from the group consisting of oxygen, sulfur, nitrogen, and phosphorus; wherein Z represents a moiety selected from the group consisting of C(R)R', oxygen, sulfur, nitrogen, and phosphorus; wherein the contiguous cyclic ring in formulas (1), (2), (3), (4), (5), (6), (7), (8), (9), and (10) can contain heteroatoms selected from the group consisting of oxygen, sulfur, nitrogen, phosphorus, and silicon in cases where m represents an integer greater than 1; wherein the contiguous cyclic ring in formulas (1), (2), (3), (4), (5), (6), (7), (8), (9), and (10) can be saturated or unsaturated in cases where m represents an integer greater than 1; wherein said alkyl groups, aryl groups, alkaryl groups, and alkoxy groups can contain halide atoms and heteroatoms selected from the group consisting of oxygen, sulfur, nitrogen, phosphorus, and silicon.

The present invention further discloses an acetal compound having a structural formula selected from the group consisting of:

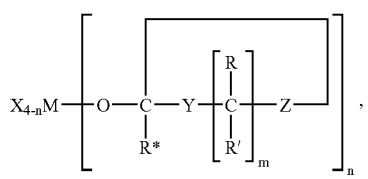

(1)

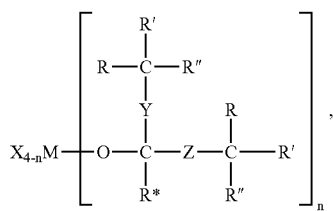

(2)

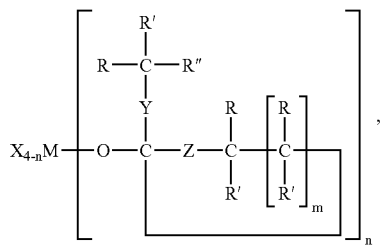

(3)

and

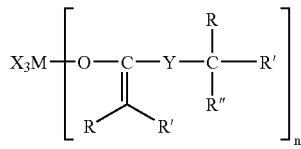

(4)

wherein M represents an atom selected from the group consisting of Ge, Sn, Pb, Ti, and Zr; wherein n represents an integer from 1 to 4; wherein m represents an integer from 1 to about 20; with the proviso that m can represent the integer 0 for structures of formula (3) wherein Z represents the group C(R)R'; wherein X groups can be the same or different; wherein X represents a chemical moiety; wherein R, R', and R" can be the same or different and are selected from the group consisting of hydrogen atoms, alkyl groups containing from 1 to about 12 carbon atoms, aryl groups containing from about 6 to about 18 carbon atoms, alkaryl groups containing from 7 to about 18 carbon atoms, alkoxy groups containing from 1 to about 18 carbon atoms, hydroxy groups, and halide atoms; wherein R* is selected from the group consisting of hydrogen atoms, alkyl groups containing from 1 to about 12 carbon atoms, aryl groups containing from about 6 to about 18 carbon atoms, and alkaryl groups containing from 7 to about 18 carbon atoms; wherein R, R', R", and R* can be bonded together in any combination in cases where R, R', R", and R* are not hydrogen atoms, halide atoms, or hydroxy groups; wherein Y represents a moiety selected from the group consisting of C(R)R', oxygen, sulfur, nitrogen, and phosphorus; wherein Z represents a moiety selected from the group consisting of C(R)R', oxygen, sulfur, nitrogen, and phosphorus; with the proviso that Y and Z can not both represent the moiety C(R)R'; wherein the contiguous cyclic ring in formulas (1) and (3) can contain heteroatoms selected from the group consisting of oxygen, sulfur, nitrogen, phosphorus, and silicon in cases where m represents an integer greater than 1; wherein the contiguous cyclic ring in formulas (1) and (3) can be saturated or unsaturated in cases where m represents an integer greater than 1; wherein said alkyl groups, aryl groups, alkaryl groups, and alkoxy groups can contain halide atoms and heteroatoms selected from the group consisting of oxygen, sulfur, nitrogen, phosphorus, and silicon.

The present invention further discloses an acetal compound having a structural formula selected from the group consisting of:

(1)

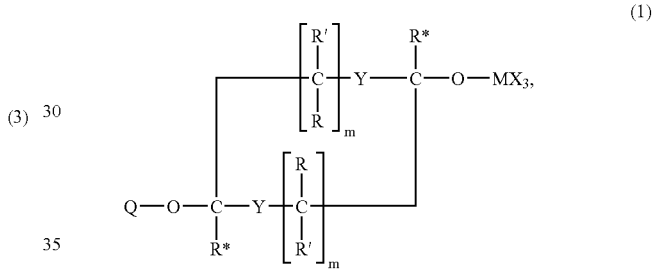

(2)

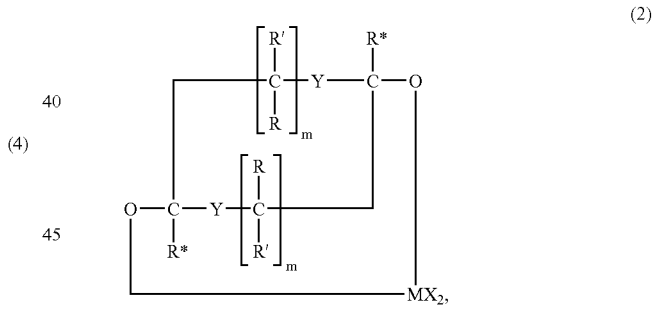

(3)

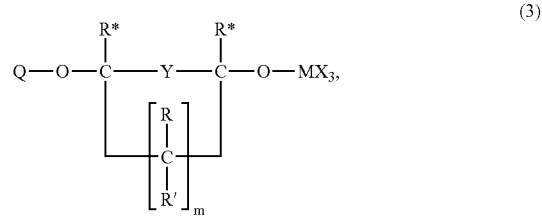

(4)

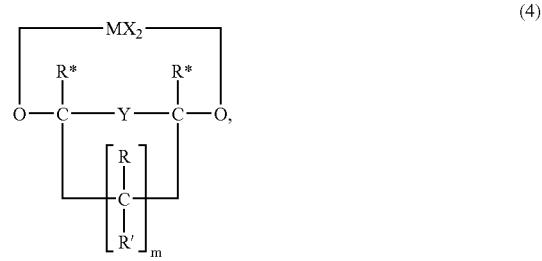

-continued

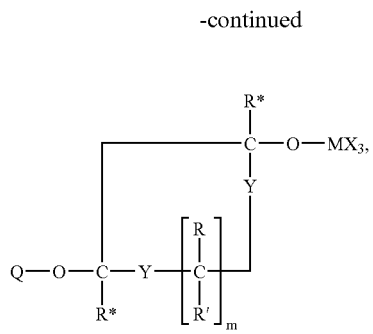
(5)

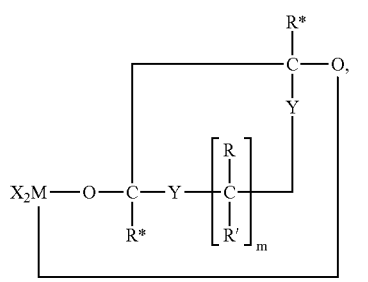
(6)

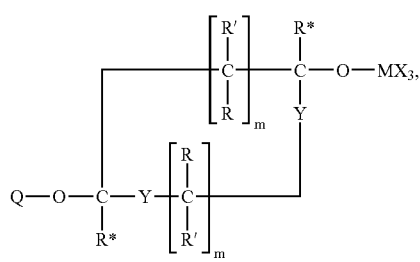
(7)

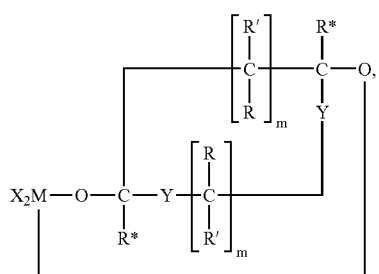
(8)

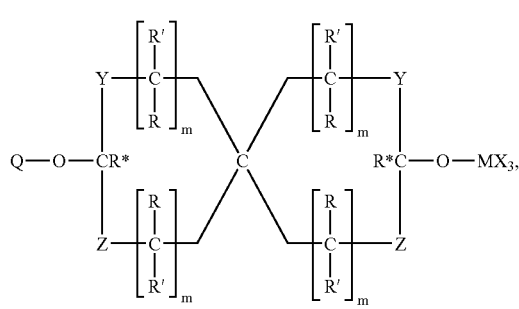
(9)

and

-continued

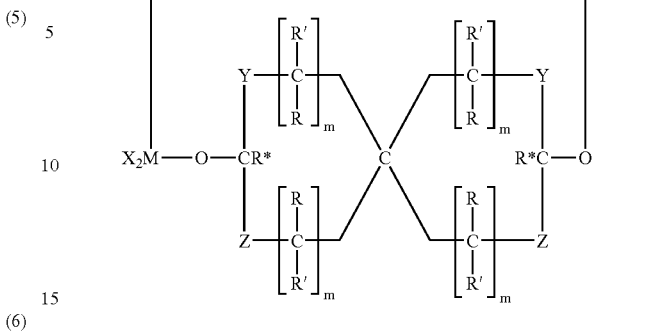
(10)

wherein M represents an atom selected from the group consisting of Ge, Sn, Pb, Ti, and Zr; wherein m represents an integer from 1 to about 20; wherein X groups can be the same or different; wherein X represents a chemical moiety; wherein Q is selected from the group consisting of hydrogen atoms and $MX_3$; wherein R and R' can be the same or different and are selected from the group consisting of hydrogen atoms, alkyl groups containing from 1 to about 12 carbon atoms, aryl groups containing from about 6 to about 18 carbon atoms, alkaryl groups containing from 7 to about 18 carbon atoms, alkoxy groups containing from 1 to about 18 carbon atoms, hydroxy groups, and halide atoms; wherein R* is selected from the group consisting of hydrogen atoms, alkyl groups containing from 1 to about 12 carbon atoms, aryl groups containing from about 6 to about 18 carbon atoms, and alkaryl groups containing from 7 to about 18 carbon atoms; wherein R, R', and R* can be bonded together in any combination in cases where R, R', and R* are not hydrogen atoms, halide atoms, or hydroxy groups; wherein Y represents a moiety selected from the group consisting of oxygen, sulfur, nitrogen, and phosphorus; wherein Z represents a moiety selected from the group consisting of C(R)R', oxygen, sulfur, nitrogen, and phosphorus; wherein the contiguous cyclic ring in formulas (1), (2), (3), (4), (5), (6), (7), (8), (9), and (10) can contain heteroatoms selected from the group consisting of oxygen, sulfur, nitrogen, phosphorus, and silicon in cases where m represents an integer greater than 1; wherein the contiguous cyclic ring in formulas (1), (2), (3), (4), (5), (6), (7), (8), (9), and (10) can be saturated or unsaturated in cases where m represents an integer greater than 1; wherein said alkyl groups, aryl groups, alkaryl groups, and alkoxy groups can contain halide atoms and heteroatoms selected from the group consisting of oxygen, sulfur, nitrogen, phosphorus, and silicon.

The present invention further discloses a process for synthesizing a modified silane which comprises reacting a cyclic hemiacetal having a structural formula selected from the group consisting of:

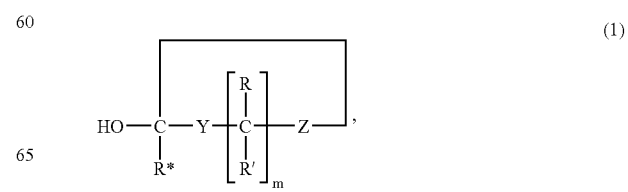
(1)

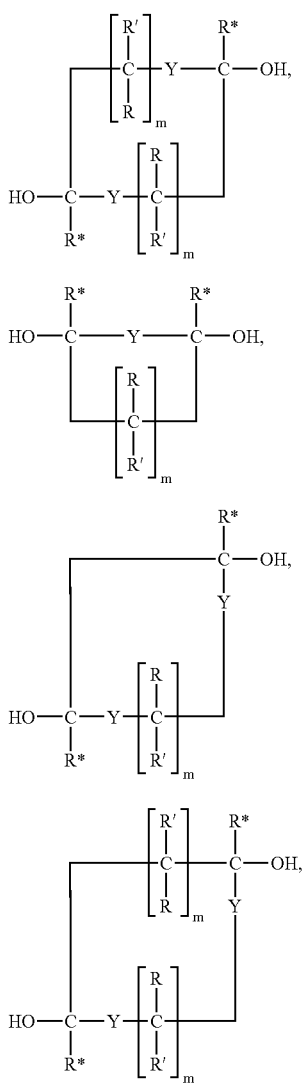

and

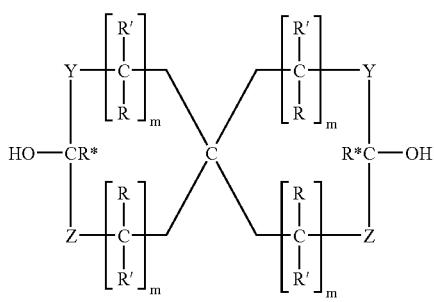

wherein m represents an integer from 1 to about 20; wherein R and R' can be the same or different and are selected from the group consisting of hydrogen atoms, alkyl groups containing from 1 to about 12 carbon atoms, aryl groups containing from about 6 to about 18 carbon atoms, alkaryl groups containing from 7 to about 18 carbon atoms, alkoxy groups containing from 1 to about 18 carbon atoms, hydroxy groups, and halide atoms; wherein R* is selected from the group consisting of hydrogen atoms, alkyl groups containing from 1 to about 12 carbon atoms, aryl groups containing from about 6 to about 18 carbon atoms, and alkaryl groups containing from 7 to about 18 carbon atoms; wherein R, R', and R* can be bonded together in any combination in cases where R, R', and R* are not hydrogen atoms, halide atoms, or hydroxy groups; wherein Y represents a moiety selected from the group consisting of oxygen, sulfur, nitrogen, and phosphorus; wherein Z represents a moiety selected from the group consisting of C(R)R', oxygen, sulfur, nitrogen, and phosphorus; wherein the contiguous cyclic ring in formulas (1), (2), (3), (4), (5), and (6) can contain heteroatoms selected from the group consisting of oxygen, sulfur, nitrogen, phosphorus, and silicon in cases where m represents an integer greater than 1; wherein the contiguous cyclic ring in formulas (1), (2), (3), (4), (5), and (6) can be saturated or unsaturated in cases where m represents an integer greater than 1; wherein said alkyl groups, aryl groups, alkaryl groups, and alkoxy groups can contain halide atoms and heteroatoms selected from the group consisting of oxygen, sulfur, nitrogen, phosphorus, and silicon; with a silicon containing compound of the structural formula:

$$X_{4-n}Si\text{-}[\text{OR}'']_n$$

wherein n represents an integer from 1 to 4; wherein R'' is selected from the group consisting of hydrogen atoms, alkyl groups containing from 1 to about 12 carbon atoms, aryl groups containing from about 6 to about 18 carbon atoms, alkaryl groups containing from 7 to about 18 carbon atoms, alkoxy groups containing from 1 to about 18 carbon atoms; wherein said alkyl groups, aryl groups, alkaryl groups, and alkoxy groups can contain halide atoms and heteroatoms selected from the group consisting of oxygen, sulfur, nitrogen, phosphorus, and silicon; wherein X represents a chemical moiety; wherein said process is conducted at a temperature which is within the range of about 10° C. to about 50° C., wherein said process is conducted at a pressure which is within the range of about 25 torr to about 75 torr, and wherein said process is conducted in the presence of an alcohol salt of the structural formula M'OR''' wherein M' represents a Group Ia metal and wherein R''' represents an alkyl group containing from 1 to 10 carbon atoms.

The present invention further discloses a process for synthesizing a modified silane which comprises reacting a cyclic hemiacetal having a structural formula selected from the group consisting of:

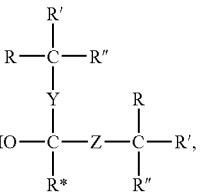

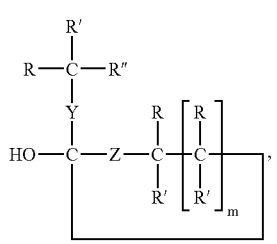

-continued and

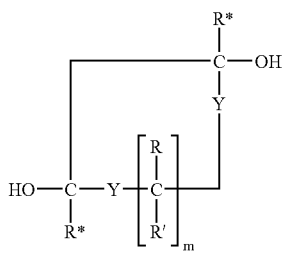
(3)

wherein m represents an integer from 1 to about 20; wherein R and R' can be the same or different and are selected from the group consisting of hydrogen atoms, alkyl groups containing from 1 to about 12 carbon atoms, aryl groups containing from about 6 to about 18 carbon atoms, alkaryl groups containing from 7 to about 18 carbon atoms, alkoxy groups containing from 1 to about 18 carbon atoms, hydroxy groups, and halide atoms; wherein R* is selected from the group consisting of hydrogen atoms, alkyl groups containing from 1 to about 12 carbon atoms, aryl groups containing from about 6 to about 18 carbon atoms, and alkaryl groups containing from 7 to about 18 carbon atoms; wherein R, R', and R* can be bonded together in any combination in cases where R, R', and R* are not hydrogen atoms, halide atoms, or hydroxy groups; wherein Y represents a moiety selected from the group consisting of oxygen, sulfur, nitrogen, and phosphorus; wherein Z represents a moiety selected from the group consisting of C(R)R', oxygen, sulfur, nitrogen, and phosphorus; wherein the contiguous cyclic ring in formulas (1), (2), (3), (4), (5), and (6) can contain heteroatoms selected from the group consisting of oxygen, sulfur, nitrogen, phosphorus, and silicon in cases where m represents an integer greater than 1; wherein the contiguous cyclic ring in formulas (1), (2), (3), (4), (5), and (6) can be saturated or unsaturated in cases where m represents an integer greater than 1; wherein said alkyl groups, aryl groups, alkaryl groups, and alkoxy groups can contain halide atoms and heteroatoms selected from the group consisting of oxygen, sulfur, nitrogen, phosphorus, and silicon; with a silicon containing compound of the structural formula:

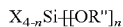

wherein n represents an integer from 1 to 4; wherein R'" is selected from the group consisting of hydrogen atoms, alkyl groups containing from 1 to about 12 carbon atoms, aryl groups containing from about 6 to about 18 carbon atoms, alkaryl groups containing from 7 to about 18 carbon atoms, alkoxy groups containing from 1 to about 18 carbon atoms; wherein said alkyl groups, aryl groups, alkaryl groups, and alkoxy groups can contain halide atoms and heteroatoms selected from the group consisting of oxygen, sulfur, nitrogen, phosphorus, and silicon; wherein X represents a chemical moiety; wherein said process is conducted at a temperature which is within the range of about 10° C. to about 50° C., wherein said process is conducted at a pressure which is within the range of about 25 torr to about 75 torr, and wherein said process is conducted in the presence of an alcohol salt of the structural formula M'OR'" wherein M' represents a Group Ia metal and wherein R'" represents an alkyl group containing from 1 to 10 carbon atoms.

The present invention further discloses a process for synthesizing a modified silane which comprises reacting a cyclic hemiacetal of the structural formula:

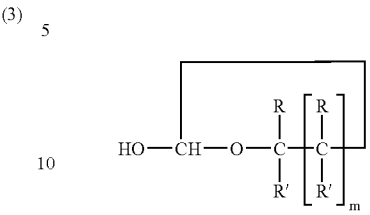

wherein R and R' can be the same or different and are selected from the group consisting of hydrogen atoms, alkyl groups containing from 1 to about 12 carbon atoms, aryl groups containing from about 6 to about 18 carbon atoms, and alkaryl groups containing from 7 to about 18 carbon atoms; with a silicon containing compound of the structural formula:

wherein n represents an integer from 1 to 4; wherein R'" represents an alkyl group containing from 1 to about 10 carbon atoms, wherein X represents a chemical moiety other than a hydrogen atom or a halogen; wherein said process is conducted at a temperature which is within the range of about 10° C. to about 50° C., wherein said process is conducted at a pressure which is within the range of about 25 torr to about 75 torr, and wherein said process is conducted in the presence of an alcohol salt of the structural formula M'OR'" wherein M' represents a Group Ia metal and wherein R'" represents an alkyl group containing from 1 to 10 carbon atoms.

The present invention further discloses a process for synthesizing a modified silane which comprises reacting a cyclic hemiacetal selected from the group consisting of tetrahydropyran-2-ol and tetrahydrofuran-2-ol; with a silicon containing compound selected from the group consisting of tetramethylorthosilicate and tetraethylorthosilicate; wherein said process is conducted at a temperature which is within the range of about 10° C. to about 50° C., wherein said process is conducted at a pressure which is within the range of about 25 torr to about 75 torr, and wherein said process is conducted in the presence of an alcohol salt of the structural formula M'OR'" wherein M' represents a Group Ia metal and wherein R'" represents an alkyl group containing from 1 to 2 carbon atoms.

The present invention further discloses a process for synthesizing a modified silane which comprises reacting a cyclic hemiacetal having a structural formula selected from the group consisting of:

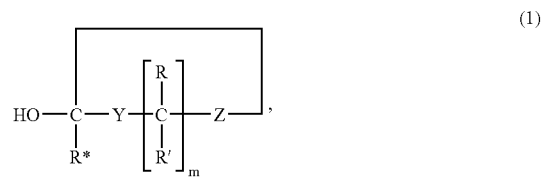
(1)

-continued

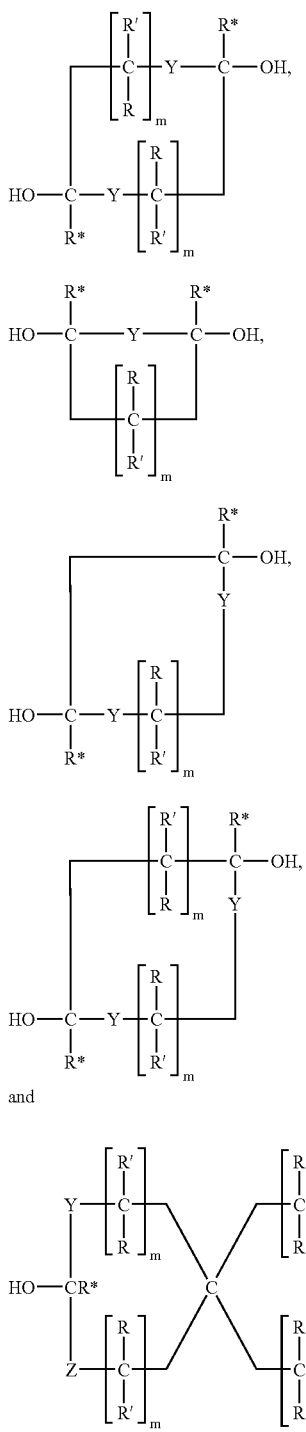

wherein m represents an integer from 1 to about 20; wherein R and R' can be the same or different and are selected from the group consisting of hydrogen atoms, alkyl groups containing from 1 to about 12 carbon atoms, aryl groups containing from about 6 to about 18 carbon atoms, alkaryl groups containing from 7 to about 18 carbon atoms, alkoxy groups containing from 1 to about 18 carbon atoms, hydroxy groups, and halide atoms; wherein R* is selected from the group consisting of hydrogen atoms, alkyl groups containing from 1 to about 12 carbon atoms, aryl groups containing from about 6 to about 18 carbon atoms, and alkaryl groups containing from 7 to about 18 carbon atoms; wherein R, R', and R* can be bonded together in any combination in cases where R, R', and R* are not hydrogen atoms, halide atoms, or hydroxy groups; wherein Y represents a moiety selected from the group consisting of oxygen, sulfur, nitrogen, and phosphorus; wherein Z represents a moiety selected from the group consisting of C(R)R', oxygen, sulfur, nitrogen, and phosphorus; wherein the contiguous cyclic ring in formulas (1), (2), (3), (4), (5), and (6) can contain heteroatoms selected from the group consisting of oxygen, sulfur, nitrogen, phosphorus, and silicon in cases where m represents an integer greater than 1; wherein the contiguous cyclic ring in formulas (1), (2), (3), (4), (5), and (6) can be saturated or unsaturated in cases where m represents an integer greater than 1; wherein said alkyl groups, aryl groups, alkaryl groups, and alkoxy groups can contain halide atoms and heteroatoms selected from the group consisting of oxygen, sulfur, nitrogen, phosphorus, and silicon; with a silicon containing compound of the structural formula:

wherein n represents an integer from 1 to 4; wherein X* represents a halide atom; wherein X represents a chemical moiety; wherein said process is conducted in the presence of an amine containing compound.

The present invention further discloses a process for synthesizing a modified silane which comprises reacting a cyclic hemiacetal having a structural formula selected from the group consisting of:

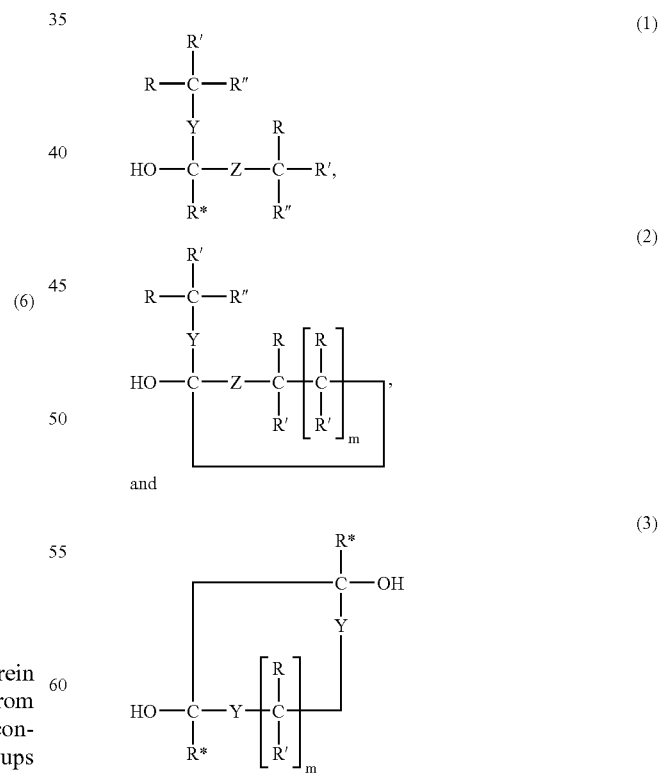

wherein m represents an integer from 1 to about 20; wherein R and R' can be the same or different and are selected from the group consisting of hydrogen atoms, alkyl groups containing from 1 to about 12 carbon atoms, aryl groups containing from about 6 to about 18 carbon atoms, alkaryl groups containing from 7 to about 18 carbon atoms, alkoxy groups containing from 1 to about 18 carbon atoms, hydroxy groups, and halide atoms; wherein R* is selected from the group consisting of hydrogen atoms, alkyl groups containing from 1 to about 12 carbon atoms, aryl groups containing from about 6 to about 18 carbon atoms, and alkaryl groups containing from 7 to about 18 carbon atoms; wherein R, R', and R* can be bonded together in any combination in cases where R, R', and R* are not hydrogen atoms, halide atoms, or hydroxy groups; wherein Y represents a moiety selected from the group consisting of oxygen, sulfur, nitrogen, and phosphorus; wherein Z represents a moiety selected from the group consisting of C(R)R', oxygen, sulfur, nitrogen, and phosphorus; wherein the contiguous cyclic ring in formulas (1), (2), (3), (4), (5), and (6) can contain heteroatoms selected from the group consisting of oxygen, sulfur, nitrogen, phosphorus, and silicon in cases where m represents an integer greater than 1; wherein the contiguous cyclic ring in formulas (1), (2), (3), (4), (5), and (6) can be saturated or unsaturated in cases where m represents an integer greater than 1; wherein said alkyl groups, aryl groups, alkaryl groups, and alkoxy groups can contain halide atoms and heteroatoms selected from the group consisting of oxygen, sulfur, nitrogen, phosphorus, and silicon; with a silicon containing compound of the structural formula:

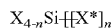

wherein n represents an integer from 1 to 4; wherein X* represents a halide atom; wherein X represents a chemical moiety; wherein said process is conducted in the presence of an amine containing compound.

The present invention further discloses a process for synthesizing a modified silane which comprises reacting a cyclic hemiacetal of the structural formula:

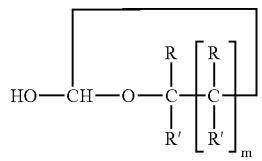

wherein R and R' can be the same or different and are selected from the group consisting of hydrogen atoms, alkyl groups containing from 1 to about 12 carbon atoms, aryl groups containing from about 6 to about 18 carbon atoms, and alkaryl groups containing from 7 to about 18 carbon atoms; with a silicon containing compound of the structural formula:

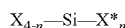

wherein n represents an integer from 1 to 4; wherein X* represents a halide atom; wherein X represents a chemical moiety; wherein said process is conducted in the presence of an amine containing compound.

22. A process for synthesizing a modified silane which comprises reacting a vinyl ether compound having a structural formula selected from the group consisting of:

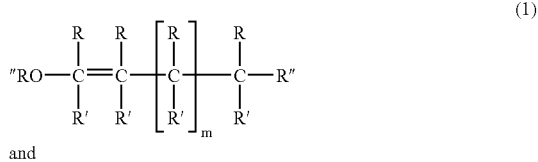

and

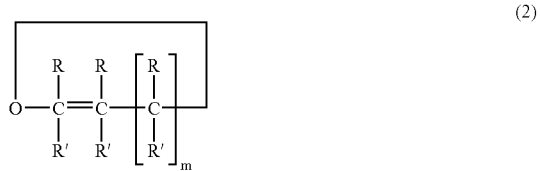

wherein m represents an integer from 1 to about 20; wherein R, R', and R" can be the same or different and are selected from the group consisting of hydrogen atoms, alkyl groups containing from 1 to about 12 carbon atoms, aryl groups containing from about 6 to about 18 carbon atoms, alkaryl groups containing from 7 to about 18 carbon atoms, alkoxy groups containing from 1 to about 18 carbon atoms, hydroxy groups, and halide atoms; wherein R, R', and R" can be bonded together in any combination in cases where R, R', and R" are not hydrogen atoms, halide atoms, or hydroxy groups; wherein the contiguous cyclic ring in formulas (2) can contain heteroatoms selected from the group consisting of oxygen, sulfur, nitrogen, phosphorus, and silicon in cases where m represents an integer greater than 1; wherein the contiguous cyclic ring in formulas (2) can be saturated or unsaturated in cases where m represents an integer greater than 1; wherein said alkyl groups, aryl groups, alkaryl groups, and alkoxy groups can contain halide atoms and heteroatoms selected from the group consisting of oxygen, sulfur, nitrogen, phosphorus, and silicon; with a silicon containing compound of the structural formula:

wherein n represents an integer from 3 to 4; wherein R* is selected from the group consisting of alkyl groups containing from 1 to about 12 carbon atoms, aryl groups containing from about 6 to about 18 carbon atoms, and alkaryl groups containing from 7 to about 18 carbon atoms; wherein said alkyl groups, aryl groups, alkaryl groups, and alkoxy groups can contain halide atoms and heteroatoms selected from the group consisting of oxygen, sulfur, nitrogen, phosphorus, and silicon; wherein X represents a chemical moiety; wherein said process is conducted in the presence of an acid.

The present invention further discloses a process for synthesizing a modified silane which comprises reacting a ester compound having a structural formula selected from the group consisting of:

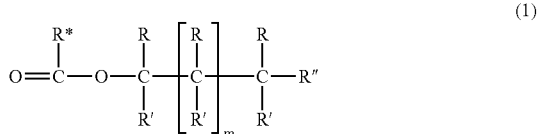

and

-continued

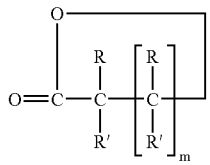
(2)

wherein m represents an integer from 1 to about 20; wherein R, R', and R" can be the same or different and are selected from the group consisting of hydrogen atoms, alkyl groups containing from 1 to about 12 carbon atoms, aryl groups containing from about 6 to about 18 carbon atoms, alkaryl groups containing from 7 to about 18 carbon atoms, alkoxy groups containing from 1 to about 18 carbon atoms, hydroxy groups, and halide atoms; wherein R* is selected from the group consisting of alkyl groups containing from 1 to about 12 carbon atoms, aryl groups containing from about 6 to about 18 carbon atoms, and alkaryl groups containing from 7 to about 18 carbon atoms; wherein R, R', R", and R* can be bonded together in any combination in cases where R, R', R", and R* are not hydrogen atoms, halide atoms, or hydroxy groups; wherein the contiguous cyclic ring in formulas (2) can contain heteroatoms selected from the group consisting of oxygen, sulfur, nitrogen, phosphorus, and silicon in cases where m represents an integer greater than 1; wherein the contiguous cyclic ring in formulas (2) can be saturated or unsaturated in cases where m represents an integer greater than 1; wherein said alkyl groups, aryl groups, alkaryl groups, and alkoxy groups can contain halide atoms and heteroatoms selected from the group consisting of oxygen, sulfur, nitrogen, phosphorus, and silicon; with a silicon containing compound of the structural formula:

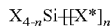

wherein n represents an integer from 2 to 4; wherein X* is leaving group selected from the group consisting of halide atoms, triflate, and tosylate; wherein X represents a chemical moiety; wherein said process is conducted in the presence of the reducing agent diisobutylaluminum hydride; wherein said process is conducted in the presence of an amine containing compound.

The present invention further discloses an aqueous polymer composition suitable for use as an adhesive, caulk, sealant, or coating which is comprised of (1) an acid; (2) a volatile base; wherein the amount of volatile base present is sufficient for the aqueous polymer composition to have a pH greater than 7; (3) water; (4) a resin having repeat units which are derived from (a) a member selected from the group consisting of vinyl monomers, vinyl aromatic monomers, conjugated diolefin monomers, and acrylic monomers, (b) a monomer in accordance of claim 7; (5) a wetting agent; (6) a defoamer; and (7) a pigment, filler, and extender; with the proviso that the aqueous polymer composition can be void of said wetting agent, defoamer, pigment, filler, and extender.

The present invention further discloses an aqueous polymer composition suitable for use as an adhesive, caulk, sealant, or coating which is comprised of (1) an acid; (2) a volatile base; wherein the amount of volatile base present is sufficient for the aqueous polymer composition to have a pH greater than 7; (3) water; (4) a resin having repeat units which are derived from (a) a member selected from the group consisting of vinyl monomers, vinyl aromatic monomers, conjugated diolefin monomers, and acrylic monomers, (b) a monomer in accordance of claim 11; (5) a wetting agent; (6) a defoamer; and (7) a pigment, filler, and extender; with the proviso that the aqueous polymer composition can be void of said wetting agent, defoamer, pigment, filler, and extender.

The present invention further discloses an aqueous polymer composition suitable for use as an adhesive, caulk, sealant, or coating which is comprised of (1) an acid; (2) a volatile base selected from the group consisting of $NR^1R^2R^3R^4OH$; wherein $R^1$, $R^2$, $R^3$, and $R^4$ can be the same or different and are selected from the group consisting of hydrogen atoms, alkyl groups containing from 1 to about 12 carbon atoms, aryl groups containing from about 6 to about 18 carbon atoms, alkaryl groups containing from 7 to about 18 carbon atoms, alkoxy groups containing from 1 to about 18 carbon atoms; $R^1$, $R^2$, $R^3$, and $R^4$ can be bonded together in any combination in cases where $R^1$, $R^2$, $R^3$, and $R^4$ are not hydrogen atoms; wherein said alkyl groups, aryl groups, alkaryl groups, and alkoxy groups can contain halide atoms and heteroatoms selected from the group consisting of oxygen, sulfur, nitrogen, phosphorus, and silicon; wherein the amount of volatile base present is sufficient for the aqueous polymer composition to have a pH greater than 7; (3) water; (4) a resin having repeat units which are derived from (a) a member selected from the group consisting of vinyl monomers, vinyl aromatic monomers, conjugated diolefin monomers, and acrylic monomers, (b) a monomer having a structural formula selected from the group consisting of:

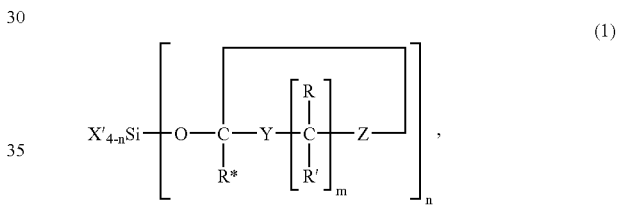
(1)

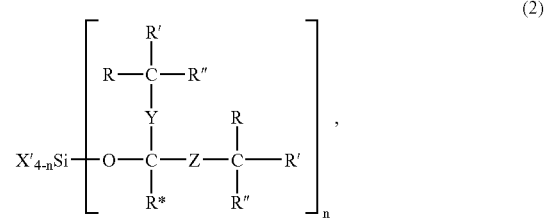
(2)

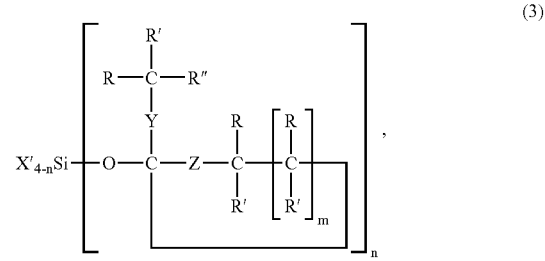
(3)

and

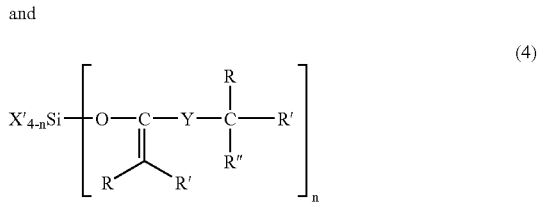
(4)

wherein n represents an integer from 1 to 3; wherein m represents an integer from 1 to about 20; with the proviso that m can represent the integer 0 for structures of formula (3) wherein Z represents the group C(R)R'; wherein X' groups can be the same or different; wherein X' represents an unsaturated moiety containing at least one non-aromatic double bond; wherein R, R', and R" can be the same or different and are selected from the group consisting of hydrogen atoms, alkyl groups containing from 1 to about 12 carbon atoms, aryl groups containing from about 6 to about 18 carbon atoms, alkaryl groups containing from 7 to about 18 carbon atoms, alkoxy groups containing from 1 to about 18 carbon atoms, hydroxy groups, and halide atoms; wherein R* is selected from the group consisting of hydrogen atoms, alkyl groups containing from 1 to about 12 carbon atoms, aryl groups containing from about 6 to about 18 carbon atoms, and alkaryl groups containing from 7 to about 18 carbon atoms; wherein R, R', R", and R* can be bonded together in any combination in cases where R, R', R", and R* are not hydrogen atoms, halide atoms, or hydroxy groups; wherein Y represents a moiety selected from the group consisting of C(R)R', oxygen, sulfur, nitrogen, and phosphorus; wherein Z represents a moiety selected from the group consisting of C(R)R', oxygen, sulfur, nitrogen, and phosphorus; with the proviso that Y and Z can not both represent the moiety C(R)R'; wherein the contiguous cyclic ring in formulas (1) and (3) can contain heteroatoms selected from the group consisting of oxygen, sulfur, nitrogen, phosphorus, and silicon in cases where m represents an integer greater than 1; wherein the contiguous cyclic ring in formulas (1) and (3) can be saturated or unsaturated in cases where m represents an integer greater than 1; wherein said alkyl groups, aryl groups, alkaryl groups, and alkoxy groups can contain halide atoms and heteroatoms selected from the group consisting of oxygen, sulfur, nitrogen, phosphorus, and silicon; (5) a wetting agent; and (6) a defoamer.

The present invention further discloses a n aqueous polymer composition suitable for use as an adhesive, caulk, sealant, or coating which is comprised of (1) an acid; (2) a volatile base selected from the group consisting of $NR^1R^2R^3R^4OH$; wherein $R^1$, $R^2$, $R^3$, and R can be the same or different and are selected from the group consisting of hydrogen atoms, alkyl groups containing from 1 to about 12 carbon atoms, aryl groups containing from about 6 to about 18 carbon atoms, alkaryl groups containing from 7 to about 18 carbon atoms, alkoxy groups containing from 1 to about 18 carbon atoms; wherein $R^1$, $R^2$, $R^3$, and $R^4$ can be bonded together in any combination in cases where $R^1$, $R^2$, $R^3$, and $R^4$ are not hydrogen atoms; wherein said alkyl groups, aryl groups, alkaryl groups, and alkoxy groups can contain halide atoms and heteroatoms selected from the group consisting of oxygen, sulfur, nitrogen, phosphorus, and silicon; wherein the amount of volatile base present is sufficient for the aqueous polymer composition to have a pH greater than 7; (3) water; (4) a resin having repeat units which are derived from (a) a member selected from the group consisting of vinyl monomers, vinyl aromatic monomers, conjugated diolefin monomers, and acrylic monomers, and (b) a monomer having a structural formula selected from the group consisting of:

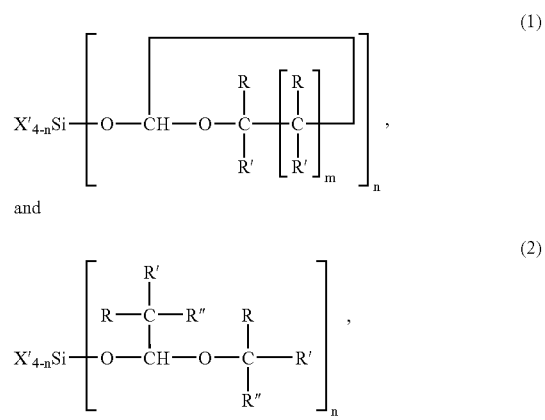

wherein n represents an integer from 1 to 3; wherein m represents an integer from 1 to about 20; wherein X' groups can be the same or different; wherein X' represents an unsaturated moiety containing at least one non-aromatic double bond; wherein R, R', and R" can be the same or different and are selected from the group consisting of hydrogen atoms, alkyl groups containing from 1 to about 12 carbon atoms, aryl groups containing from about 6 to about 18 carbon atoms, alkaryl groups containing from 7 to about 18 carbon atoms, alkoxy groups containing from 1 to about 18 carbon atoms, hydroxy groups, and halide atoms; wherein R, R', and R" can be bonded together in any combination in cases where R, R', and R" are not hydrogen atoms, halide atoms, or hydroxy groups; wherein the contiguous cyclic ring in formula (1) can contain heteroatoms selected from the group consisting of oxygen, sulfur, nitrogen, phosphorus, and silicon in cases where m represents an integer greater than 1; wherein the contiguous cyclic ring in formula (1) can be saturated or unsaturated in cases where m represents an integer greater than 1; wherein said alkyl groups, aryl groups, alkaryl groups, and alkoxy groups can contain halide atoms and heteroatoms selected from the group consisting of oxygen, sulfur, nitrogen, phosphorus, and silicon; (5) a wetting agent; and (6) a defoamer.

The present invention further discloses an aqueous polymer composition suitable for use as an adhesive, caulk, sealant, or coating which is comprised of (1) an acid (2) a volatile base selected from the group consisting of $NR^1R^2R^3R^4OH$; wherein $R^1$, $R^2$, $R^3$, and $R^4$ can be the same or different and are selected from the group consisting of hydrogen atoms, alkyl groups containing from 1 to about 12 carbon atoms, aryl groups containing from about 6 to about 18 carbon atoms, alkaryl groups containing from 7 to about 18 carbon atoms, alkoxy groups containing from 1 to about 18 carbon atoms; wherein $R^1$, $R^2$, $R^3$, and $R^4$ can be bonded together in any combination in cases $R^1$, $R^2$, $R^3$, and $R^4$ are not hydrogen atoms; wherein said alkyl groups, aryl groups, alkaryl groups, and alkoxy groups can contain halide atoms and heteroatoms selected from the group consisting of oxygen, sulfur, nitrogen, phosphorus, and silicon; wherein the amount of volatile base present is sufficient for the aqueous polymer composition to have a pH greater than 7; (3) water; (4) a resin having repeat units which are derived from (a) a member selected from the group consisting of vinyl monomers, vinyl aromatic monomers, conjugated diolefin monomers, and acrylic monomers, and (b) a monomer consisting of the following structure:

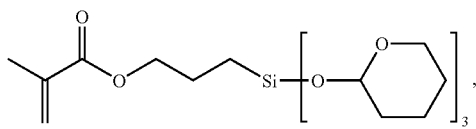

and (5) a wetting agent; and (6) a defoamer.

The present invention further discloses an organic solvent based polymer composition suitable for use as an adhesive, caulk, sealant, or coating which is comprised of (1) an organic solvent; (2) an acid; (3) a volatile base selected from the group consisting of $NR^1R^2R^3R^4OH$; wherein $R^1$, $R^2$, $R^3$, and $R^4$ can be the same or different and are selected from the group consisting of hydrogen atoms, alkyl groups containing from 1 to about 12 carbon atoms, aryl groups containing from about 6 to about 18 carbon atoms, alkaryl groups containing from 7 to about 18 carbon atoms, alkoxy groups containing from 1 to about 18 carbon atoms; wherein $R^1$, $R^2$, $R^3$, and $R^4$ can be bonded together in any combination in cases where $R^1$, $R^2$, $R^3$, and $R^4$ are not hydrogen atoms; wherein said alkyl groups, aryl groups, alkaryl groups, and alkoxy groups can contain halide atoms and heteroatoms selected from the group consisting of oxygen, sulfur, nitrogen, phosphorus, and silicon; wherein the amount of volatile base present is sufficient for the organic solvent based polymer composition to be rendered basic; (4) a resin having repeat units which are derived from (a) a member selected from the group consisting of vinyl monomers, vinyl aromatic monomers, conjugated diolefin monomers, and acrylic monomers, and (b) a monomer having a structural formula selected from the group consisting of:

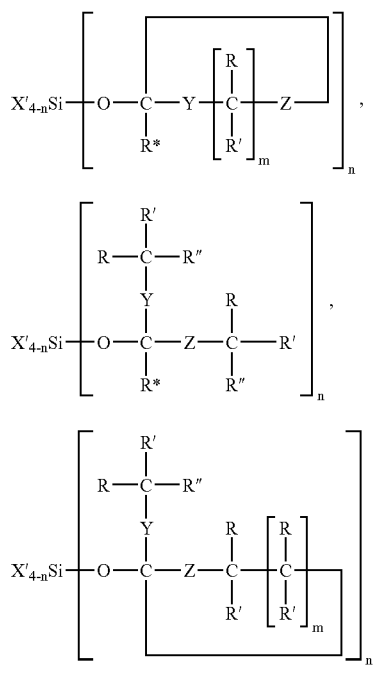

and

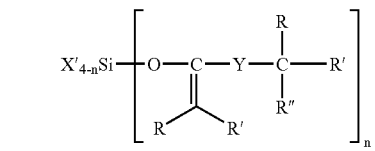

wherein n represents an integer from 1 to 3; wherein m represents an integer from 1 to about 20; with the proviso that m can represent the integer 0 for structures of formula (3) wherein Z represents the group C(R)R'; wherein X' groups can be the same or different; wherein X' represents an unsaturated moiety containing at least one non-aromatic double bond; wherein R, R', and R" can be the same or different and are selected from the group consisting of hydrogen atoms, alkyl groups containing from 1 to about 12 carbon atoms, aryl groups containing from about 6 to about 18 carbon atoms, alkaryl groups containing from 7 to about 18 carbon atoms, alkoxy groups containing from 1 to about 18 carbon atoms, hydroxy groups, and halide atoms; wherein R* is selected from the group consisting of hydrogen atoms, alkyl groups containing from 1 to about 12 carbon atoms, aryl groups containing from about 6 to about 18 carbon atoms, and alkaryl groups containing from 7 to about 18 carbon atoms; wherein R, R', R", and R* can be bonded together in any combination in cases where R, R', R", and R* are not hydrogen atoms, halide atoms, or hydroxy groups; wherein Y represents a moiety selected from the group consisting of C(R)R', oxygen, sulfur, nitrogen, and phosphorus; wherein Z represents a moiety selected from the group consisting of C(R)R', oxygen, sulfur, nitrogen, and phosphorus; with the proviso that Y and Z can not both represent the moiety C(R)R'; wherein the contiguous cyclic ring in formulas (1) and (3) can contain heteroatoms selected from the group consisting of oxygen, sulfur, nitrogen, phosphorus, and silicon in cases where m represents an integer greater than 1; wherein the contiguous cyclic ring in formulas (1) and (3) can be saturated or unsaturated in cases where m represents an integer greater than 1; wherein said alkyl groups, aryl groups, alkaryl groups, and alkoxy groups can contain halide atoms and heteroatoms selected from the group consisting of oxygen, sulfur, nitrogen, phosphorus, and silicon; (5) a wetting agent; and (6) a defoamer.

The present invention further discloses an organic solvent based polymer composition suitable for use as an adhesive, caulk, sealant, or coating which is comprised of (1) an organic solvent; (2) an acid; (3) a volatile base selected from the group consisting $NR^1R^2R^3R^4OH$; wherein $R^1$, $R^2$, $R^3$, and $R^4$ can be the same or different and are selected from the group consisting of hydrogen atoms, alkyl groups containing from 1 to about 12 carbon atoms, aryl groups containing from about 6 to about 18 carbon atoms, alkaryl groups containing from 7 to about 18 carbon atoms, alkoxy groups containing from 1 to about 18 carbon atoms; wherein $R^1$, $R^2$, $R^3$, and $R^4$ can be bonded together in any combination in cases where $R^1$, $R^2$, $R^3$, and $R^4$ are not hydrogen atoms; wherein said alkyl groups, aryl groups, alkaryl groups, and alkoxy groups can contain halide atoms and heteroatoms selected from the group consisting of oxygen, sulfur, nitrogen, phosphorus, and silicon; wherein the amount of volatile base present is sufficient for the organic solvent based polymer composition to be rendered basic; (4) a resin having repeat units which are derived from (a) a member selected from the group consisting of vinyl monomers, vinyl aromatic monomers, conjugated diolefin monomers, and acrylic monomers, and (b) a monomer having a structural formula selected from the group consisting of:

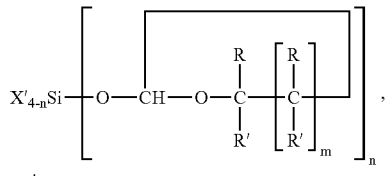
(1)

and

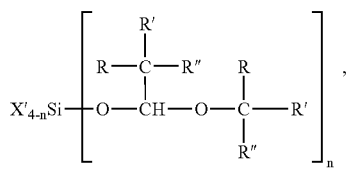
(2)

wherein n represents an integer from 1 to 3; wherein m represents an integer from 1 to about 20; wherein X' groups can be the same or different; wherein X' represents an unsaturated moiety containing at least one non-aromatic double bond; wherein R, R', and R" can be the same or different and are selected from the group consisting of hydrogen atoms, alkyl groups containing from 1 to about 12 carbon atoms, aryl groups containing from about 6 to about 18 carbon atoms, alkaryl groups containing from 7 to about 18 carbon atoms, alkoxy groups containing from 1 to about 18 carbon atoms, hydroxy groups, and halide atoms; wherein R, R', and R" can be bonded together in any combination in cases where R, R', and R" are not hydrogen atoms, halide atoms, or hydroxy groups; wherein the contiguous cyclic ring in formula (1) can contain heteroatoms selected from the group consisting of oxygen, sulfur, nitrogen, phosphorus, and silicon in cases where m represents an integer greater than 1; wherein the contiguous cyclic ring in formula (1) can be saturated or unsaturated in cases where m represents an integer greater than 1; wherein said alkyl groups, aryl groups, alkaryl groups, and alkoxy groups can contain halide atoms and heteroatoms selected from the group consisting of oxygen, sulfur, nitrogen, phosphorus, and silicon; (5) a wetting agent; and (6) defoamer.

The present invention further discloses an organic solvent based polymer composition suitable for use as an adhesive, caulk, sealant, or coating which is comprised of (1) an organic solvent; (2) an acid; (3) a volatile base selected from the group consisting of $NR^1R^2R^3R^4OH$; wherein $R^1$, $R^2$, $R^3$, and $R^4$ can be the same or different and are selected from the group consisting of hydrogen atoms, alkyl groups containing from 1 to about 12 carbon atoms, aryl groups containing from about 6 to about 18 carbon atoms, alkaryl groups containing from 7 to about 18 carbon atoms, alkoxy groups containing from 1 to about 18 carbon atoms; wherein $R^1$, $R^2$, $R^3$, and $R^4$ can be bonded together in any combination in cases where $R^1$, $R^2$, $R^3$, and $R^4$ are not hydrogen atoms; wherein said alkyl groups, aryl groups, alkaryl groups, and alkoxy groups can contain halide atoms and heteroatoms selected from the group consisting of oxygen, sulfur, nitrogen, phosphorus, and silicon; wherein the amount of volatile base present is sufficient for the organic solvent based polymer composition to be rendered basic; (4) a resin having repeat units which are derived from (a) a member selected from the group consisting of vinyl monomers, vinyl aromatic monomers, conjugated diolefin monomers, and acrylic monomers, and (b) a monomer consisting of the following structure:

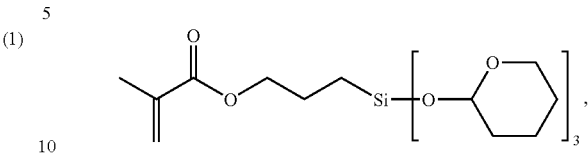
(5)

and (5) a wetting agent; and (6) a defoamer.

The present invention further discloses a one-component condensation-crosslinking room-temperature vulcanizable silicone rubber composition comprising (1) silanol end-terminated organopolysiloxane base polymer; (2) modified silane compound of claim 3; (3) an acid; (4) a volatile base selected from the group consisting $NR^1R^2R^3R^4OH$; wherein $R^1$, $R^2$, $R^3$, and $R^4$ can be the same or different and are selected from the group consisting of hydrogen atoms, alkyl groups containing from 1 to about 12 carbon atoms, aryl groups containing from about 6 to about 18 carbon atoms, alkaryl groups containing from 7 to about 18 carbon atoms, alkoxy groups containing from 1 to about 18 carbon atoms; wherein $R^1$, $R^2$, $R^3$, and $R^4$ can be bonded together in any combination in cases where $R^1$, $R^2$, $R^3$, and $R^4$ are not hydrogen atoms; wherein said alkyl groups, aryl groups, alkaryl groups, and alkoxy groups can contain halide atoms and heteroatoms selected from the group consisting of oxygen, sulfur, nitrogen, phosphorus, and silicon; wherein the amount of volatile base present is sufficient to render the one-component condensation-crosslinking room-temperature vulcanizable silicone rubber composition basic; and (5) a reinforcing particulate filler.

The present invention further discloses a one-component condensation-crosslinking room-temperature vulcanizable silicone rubber composition comprising (1) silanol end-terminated organopolysiloxane base polymer; (2) modified silane compound of claim 9; (3) an acid; (4) a volatile base selected from the group consisting $NR^1R^2R^3R^4OH$; wherein $R^1$, $R^2$, $R^3$, and $R^4$ can be the same or different and are selected from the group consisting of hydrogen atoms, alkyl groups containing from 1 to about 12 carbon atoms, aryl groups containing from about 6 to about 18 carbon atoms, alkaryl groups containing from 7 to about 18 carbon atoms, alkoxy groups containing from 1 to about 18 carbon atoms; wherein $R^1$, $R^2$, $R^3$, and $R^4$ can be bonded together in any combination in cases where $R^1$, $R^2$, $R^3$, and $R^4$ are not hydrogen atoms; wherein said alkyl groups, aryl groups, alkaryl groups, and alkoxy groups can contain halide atoms and heteroatoms selected from the group consisting of oxygen, sulfur, nitrogen, phosphorus, and silicon; wherein the amount of volatile base present is sufficient to render the one-component condensation-crosslinking room-temperature vulcanizable silicone rubber composition basic; and (5) a reinforcing particulate filler.

The present invention further discloses a one-component condensation-crosslinking room-temperature vulcanizable silicone rubber composition comprising (1) silanol end-terminated organopolysiloxane base polymer; (2) modified silane compound of claim 12 and claim 13; (3) an acid; (4) a volatile base selected from the group consisting $NR^1R^2R^3R^4OH$; wherein $R^1$, $R^2$, $R^3$, and $R^4$ can be the same or different and are selected from the group consisting of hydrogen atoms, alkyl groups containing from 1 to about 12 carbon atoms, aryl groups containing from about 6 to about 18 carbon atoms, alkaryl groups containing from 7 to about 18 carbon atoms, alkoxy groups containing from 1 to about 18 carbon atoms; wherein $R^1$, $R^2$, $R^3$, and $R^4$ can be bonded together in any combination in cases where $R^1$, $R^2$, $R^3$, and $R^4$ are not hydrogen atoms; wherein said alkyl groups, aryl groups, alkaryl groups, and alkoxy groups can contain halide atoms and heteroatoms selected from the group consisting of oxygen, sulfur, nitrogen, phosphorus, and silicon; wherein the amount of volatile base present is sufficient to render the one-component condensation-crosslinking room-temperature vulcanizable silicone rubber composition basic; and (5) a reinforcing particulate filler.

The present invention also reveals a process for synthesizing a modified silane which comprises reacting the salt of a cyclic hemiacetal having a structural formula selected from the group consisting of:

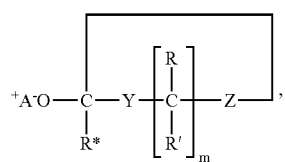
(1)

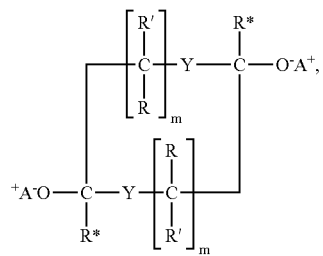
(2)

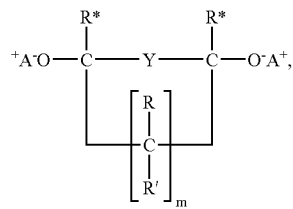
(3)

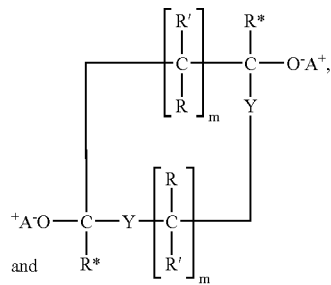
(4)

and

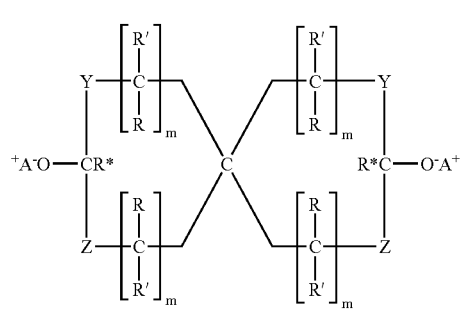
(5)

wherein A represents an alkali metal atom selected from the group consisting of lithium, sodium, and potassium; wherein m represents an integer from 1 to about 20; wherein R and R' can be the same or different and are selected from the group consisting of hydrogen atoms, alkyl groups containing from 1 to about 12 carbon atoms, aryl groups containing from about 6 to about 18 carbon atoms, alkaryl groups containing from 7 to about 18 carbon atoms, and alkoxy groups containing from 1 to about 18 carbon atoms; wherein R* is selected from the group consisting of hydrogen atoms, alkyl groups containing from 1 to about 12 carbon atoms, aryl groups containing from about 6 to about 18 carbon atoms, and alkaryl groups containing from 7 to about 18 carbon atoms; wherein R, R', and R* can be bonded together in any combination in cases where R, R', and R* are not hydrogen atoms; wherein Y represents a moiety selected from the group consisting of oxygen, sulfur, nitrogen, and phosphorus; wherein Z represents a moiety selected from the group consisting of C(R)R', oxygen, sulfur, nitrogen, and phosphorus; wherein the contiguous cyclic ring in formulas (1), (2), (3), (4), and (5) can contain heteroatoms selected from the group consisting of oxygen, sulfur, nitrogen, phosphorus, and silicon in cases where m represents an integer greater than 1; wherein the contiguous cyclic ring in formulas (1), (2), (3), (4), and (5) can be saturated or unsaturated in cases where m represents an integer greater than 1; wherein said alkyl groups, aryl groups, alkaryl groups, and alkoxy groups can contain heteroatoms selected from the group consisting of oxygen, sulfur, nitrogen, phosphorus, and silicon; with a silicon containing compound of the structural formula:

$$R''_{4-n}SiA'_n$$

wherein n represents an integer from 1 to 4; wherein R" is selected from the group consisting of hydrogen atoms, alkyl groups containing from 1 to about 12 carbon atoms, aryl groups containing from about 6 to about 18 carbon atoms, alkaryl groups containing from 7 to about 18 carbon atoms, alkoxy groups containing from 1 to about 18 carbon atoms; wherein said alkyl groups, aryl groups, alkaryl groups, and alkoxy groups can contain heteroatoms selected from the group consisting of oxygen, sulfur, nitrogen, phosphorus, and silicon; wherein A' represents a halide atom selected from the group consisting of fluorine, chlorine, bromine, and iodine; wherein said process is conducted at a temperature which is within the range of about $-100°$ C. to about $50°$ C.

The subject invention further discloses a process for synthesizing a modified silane which comprises reacting the salt of a hemiacetal having a structural formula selected from the group consisting of:

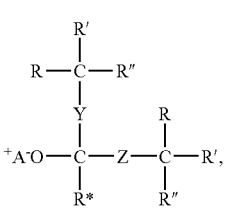
(1)

-continued

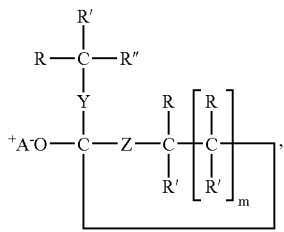

(2)

and

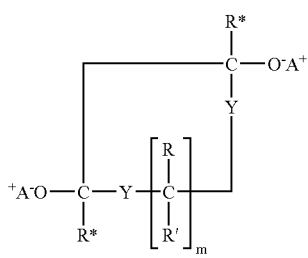

(3)

wherein A represents an alkali metal atom selected from the group consisting of lithium, sodium, and potassium; wherein m represents an integer from 1 to about 20; wherein R and R' can be the same or different and are selected from the group consisting of hydrogen atoms, alkyl groups containing from 1 to about 12 carbon atoms, aryl groups containing from about 6 to about 18 carbon atoms, alkaryl groups containing from 7 to about 18 carbon atoms, and alkoxy groups containing from 1 to about 18 carbon atoms; wherein R* is selected from the group consisting of hydrogen atoms, alkyl groups containing from 1 to about 12 carbon atoms, aryl groups containing from about 6 to about 18 carbon atoms, and alkaryl groups containing from 7 to about 18 carbon atoms; wherein R, R', and R* can be bonded together in any combination in cases where R, R', and R* are not hydrogen atoms; wherein Y represents a moiety selected from the group consisting of oxygen, sulfur, nitrogen, and phosphorus; wherein Z represents a moiety selected from the group consisting of C(R)R', oxygen, sulfur, nitrogen, and phosphorus; wherein the contiguous cyclic ring in formulas (1), (2), and (3) can contain heteroatoms selected from the group consisting of oxygen, sulfur, nitrogen, phosphorus, and silicon in cases where m represents an integer greater than 1; wherein the contiguous cyclic ring in formulas (1), (2), and (3) can be saturated or unsaturated in cases where m represents an integer greater than 1; wherein said alkyl groups, aryl groups, alkaryl groups, and alkoxy groups can contain heteroatoms selected from the group consisting of oxygen, sulfur, nitrogen, phosphorus, and silicon; with a silicon containing compound of the structural formula:

$R''_{4-n}SiA'_n$ wherein n represents an integer from 1 to 4; wherein R" is selected from the group consisting of hydrogen atoms, alkyl groups containing from 1 to about 12 carbon atoms, aryl groups containing from about 6 to about 18 carbon atoms, alkaryl groups containing from 7 to about 18 carbon atoms, alkoxy groups containing from 1 to about 18 carbon atoms; wherein said alkyl groups, aryl groups, alkaryl groups, and alkoxy groups can contain heteroatoms selected from the group consisting of oxygen, sulfur, nitrogen, phosphorus, and silicon; wherein A' represents a halide atom selected from the group consisting of fluorine, chlorine, bromine, and iodine; wherein said process is conducted at a temperature which is within the range of about −100° C. to about 50° C.

The present invention also reveals a process for synthesizing a modified silane which comprises reacting the salt of a cyclic hemiacetal of the structural formula:

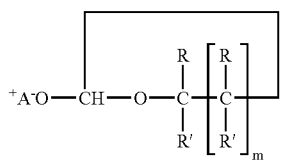

wherein A represents an alkali metal atom selected from the group consisting of lithium, sodium, and potassium; wherein R and R' can be the same or different and are selected from the group consisting of hydrogen atoms, alkyl groups containing from 1 to about 12 carbon atoms, aryl groups containing from about 6 to about 18 carbon atoms, and alkaryl groups containing from 7 to about 18 carbon atoms; with a silicon containing compound of the structural formula:

$R''_{4-n}SiA'_n$ wherein n represents an integer from 1 to 4; wherein R" represents an alkyl group containing from 1 to about 10 carbon atoms; wherein A' represents a halide atom selected from the group consisting of fluorine, chlorine, bromine, and iodine; wherein said process is conducted at a temperature which is within the range of about −100° C. to about 50° C.

The subject invention also discloses a process for synthesizing a modified silane which comprises reacting the sodium salt tetrahydropyran-2-ol; with silicon tetrachloride; wherein said process is conducted at a temperature which is within the range of about −100° C. to about 50° C.

The present invention further discloses a process for synthesizing the alkali metal salt of a cyclic hemiacetal which comprises reacting the cyclic hemiacetal with an alkali metal compound having a structural formula selected from the group consisting of:

$R**M*$ wherein M* is an alkali metal selected from the group consisting of Li, Na, and K; wherein R** is selected from the group consisting of hydrogen atoms, alkyl groups containing from 1 to about 12 carbon atoms, aryl groups containing from about 6 to about 18 carbon atoms, and alkaryl groups containing from 7 to about 18 carbon atoms; wherein said alkyl groups, aryl groups, and alkaryl groups can contain heteroatoms selected from the group consisting of oxygen, sulfur, nitrogen, phosphorus, and silicon; wherein said process is conducted in the absence of protic solvents selected from the group consisting of R"OH; wherein R" is selected from the group consisting of hydrogen atoms, alkyl groups containing from 1 to about 12 carbon atoms, aryl groups containing from about 6 to about 18 carbon atoms, and alkaryl groups containing from 7 to about 18 carbon atoms; wherein said alkyl groups, aryl groups, and alkaryl groups can contain heteroatoms selected from the group consisting of oxygen, sulfur, nitrogen, phosphorus, and silicon; wherein said process is conducted at a temperature which is within the range of about −100° C. to about 100° C.

The subject invention also discloses a process for synthesizing the sodium salt of a cyclic hemiacetal which comprises reacting the cyclic hemiacetal with sodium hydride; wherein said process is conducted in the absence of protic solvents selected from the group consisting of R"OH; wherein R" is selected from the group consisting of hydrogen atoms, alkyl groups containing from 1 to about 12 carbon atoms, aryl groups containing from about 6 to about 18 carbon atoms, and alkaryl groups containing from 7 to about 18 carbon atoms; wherein said alkyl groups, aryl groups, and alkaryl groups can contain heteroatoms selected from the group consisting of oxygen, sulfur, nitrogen, phosphorus, and silicon; wherein said process is conducted at a temperature which is within the range of about −100° C. to about 100° C.

The subject invention also reveals a process for synthesizing the sodium salt of tetrahydropyran-2-ol which comprises reacting tetrahydropyran-2-ol with sodium hydride; wherein said process is conducted in the absence of protic solvents selected from the group consisting of R"OH; wherein R" is selected from the group consisting of hydrogen atoms, alkyl groups containing from 1 to about 12 carbon atoms, aryl groups containing from about 6 to about 18 carbon atoms, and alkaryl groups containing from 7 to about 18 carbon atoms; wherein said alkyl groups, aryl groups, and alkaryl groups can contain heteroatoms selected from the group consisting of oxygen, sulfur, nitrogen, phosphorus, and silicon; wherein said process is conducted at a temperature which is within the range of about −100° C. to about 100° C.

DETAILED DESCRIPTION OF THE SYNTHESIS OF A COATING RESIN

The coating resins of this invention are prepared by free radical emulsion polymerization. The charge compositions used in the preparation of the latices of the coating resins contain monomers, at least one emulsifier (soap), such as an α-olefin sulfonate surfactant, and at least one free radical initiator. The monomer charge composition used in such polymerizations will typically be comprised of (a) from about 30 to about 75 weight percent vinyl aromatic monomers, (b) from about 20 to about 65 weight percent of alkyl acrylate monomers, (c) from about 1 to about 8 weight percent alkyl propenoic acid monomers, and (d) about 0.5 to about 5 weight percent of a reversibly protected silane monomer.

It is preferred for the polymer being synthesized to be comprised of from about 40 weight percent to about 70 weight percent vinyl aromatic monomers, from about 25 weight percent to about 55 weight percent alkyl acrylate monomers, from about 1.5 weight percent to about 5 weight percent alkyl propenoic acid monomers and from about 1 weight percent to about 3 weight percent of a reversibly protected silane monomer. It is more preferred for the polymer to be comprised of from about 63 weight percent to about 67 weight percent vinyl aromatic monomers, from about 27 weight percent to about 31 weight percent alkyl acrylate monomers, from about 2 weight percent to about 4 weight percent alkyl propenoic acid monomers, and from about 1.5 weight percent to about 2 weight percent reversibly protected silane monomers.

Some representative examples of vinyl aromatic monomers which can be used include styrene, alpha-methyl styrene and vinyl toluene. Styrene and alpha-methyl styrene are the preferred vinyl aromatic monomers. Due to its relatively low cost, styrene is the most preferred vinyl aromatic monomer.

The alkyl acrylate monomers which can be employed have alkyl moieties which contain from 2 to about 10 carbon atoms. The alkyl acrylate monomer will preferably have an alkyl moiety that contains from 3 to 5 carbon atoms. Normal-butyl acrylate is a highly preferred alkyl acrylate monomer.

The alkyl propenoic acid monomers that can be used have the structural formula:

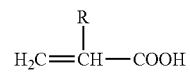

wherein R represents a hydrogen atom or an alkyl group containing from 1 to 4 carbon atoms. The R group can accordingly be represented by the formula $-C_nH_{2n+1}$ wherein n is an integer from 0 to 4. Some representative examples of alkyl propenoic acid monomers which can be used include: acrylic acid, methacrylic acid (2-methylpropenoic acid), 2-ethylpropenoic acid, 2-propylpropenoic acid and 2-butylpropenoic acid. The preferred alkyl propenoic acid monomers are acrylic acid and methacrylic acid.

In most cases, it is advantageous to use a combination of both acrylic acid and methacrylic acid as the unsaturated carbonyl compound component used in making the latex. For instance, the utilization of about 1 to about 3 weight percent acrylic acid with about 0.5 to about 1.5 weight percent methacrylic acid results in the latex having improved freeze-thaw stability. For example, the utilization of about 2 percent acrylic acid with 1 percent methacrylic acid as the unsaturated carbonyl compound component results in the latex produced being capable of withstanding more than five (5) freeze-thaw cycles. It is important for latices which are shipped through cold regions of the world to have this improved freeze-thaw stability.

The reversibly protected silane monomers that can be used are of a structural formula selected from the group consisting of:

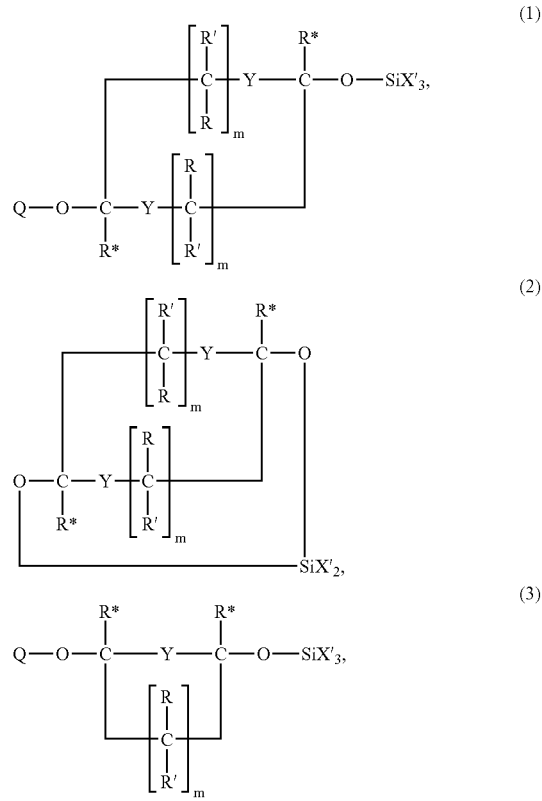

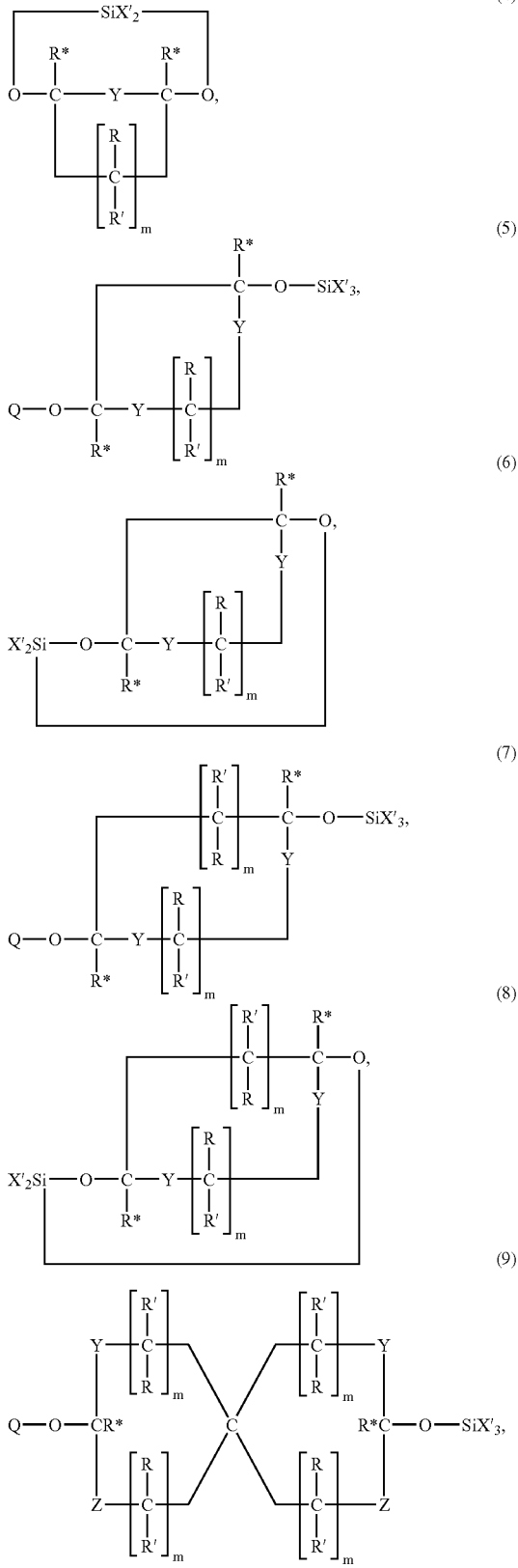

wherein m represents an integer from 1 to about 20; wherein X' groups can be the same or different; wherein X' represents an unsaturated moiety containing at least one non-aromatic double bond; wherein Q is selected from the group consisting of hydrogen atoms and $SiX'_3$; wherein R and R' can be the same or different and are selected from the group consisting of hydrogen atoms, alkyl groups containing from 1 to about 12 carbon atoms, aryl groups containing from about 6 to about 18 carbon atoms, alkaryl groups containing from 7 to about 18 carbon atoms, alkoxy groups containing from 1 to about 18 carbon atoms, hydroxy groups, and halide atoms; wherein R* is selected from the group consisting of hydrogen atoms, alkyl groups containing from 1 to about 12 carbon atoms, aryl groups containing from about 6 to about 18 carbon atoms, and alkaryl groups containing from 7 to about 18 carbon atoms; wherein R, R', and R* can be bonded together in any combination in cases where R, R', and R* are not hydrogen atoms, halide atoms, or hydroxy groups; wherein Y represents a moiety selected from the group consisting of oxygen, sulfur, nitrogen, and phosphorus; wherein Z represents a moiety selected from the group consisting of C(R)R', oxygen, sulfur, nitrogen, and phosphorus; wherein the contiguous cyclic ring in formulas (1), (2), (3), (4), (5), (6), (7), (8), (9), and (10) can contain heteroatoms selected from the group consisting of oxygen, sulfur, nitrogen, phosphorus, and silicon in cases where m represents an integer greater than 1; wherein the contiguous cyclic ring in formulas (1), (2), (3), (4), (5), (6), (7), (8), (9), and (10) can be saturated or unsaturated in cases where m represents an integer greater than 1; wherein said alkyl groups, aryl groups, alkaryl groups, and alkoxy groups can contain halide atoms and heteroatoms selected from the group consisting of oxygen, sulfur, nitrogen, phosphorus, and silicon.

Some specific examples of reversibly protected silane monomers that can be used include 3-methacryloxypropyl-silane tri-acetal and vinylmethylsilane diacetal.

The charge composition used in the preparation of the latice will contain a substantial quantity of water. The ratio between the total amount of monomers present in the charge composition and water can range between about 0.2:1 and about 1.2:1. It is generally preferred for the ratio of monomers to water in the charge composition to be within the range of about 0.8:1 and about 1.1:1. For instance, it is very satisfactory to utilize a ratio of monomers to water in the charge composition of about 1:1.

The charge composition will also typically contain from about 0.2 phm (parts per hundred parts of monomer) to about 3 phm of at least one emulsifier (soap), such as an α-olefin sulfonate soap. It is normally preferred for α-olefin sulfonate surfactants to be present in the polymerization medium at a level within the range of about 0.4 phm to about 2 phm. It is generally more preferred for the charge composition to contain from about 0.5 phm to about 1 phm of the α-olefin sulfonate soap.

The use of larger amounts of the α-olefin sulfonate soap in the polymerization medium leads to better latex stability. However, the utilization of larger amounts of surfactant also leads to greater blushing in the ultimate coating and consequently less rust and corrosion resistance.

The free radical aqueous emulsion polymerizations used in preparing the latice is typically initiated with at least one free radical generator. The free radical generator is normally employed at a concentration within the range of about 0.01 phm to about 1 phm. The free radical initiators which are commonly used include the various peroxygen compounds such as potassium persulfate, ammonium persulfate, benzoyl peroxide, hydrogen peroxide, di-t-butyl peroxide, dicumyl peroxide, 2,4-dichlorobenzoyl peroxide, decanoyl peroxide, lauryl peroxide, cumene hydroperoxide, p-menthane hydroperoxide, t-butyl hydroperoxide, acetyl peroxide, methyl ethyl ketone peroxide, succinic acid peroxide, dicetyl peroxydicarbonate, t-butyl peroxyacetate, t-butyl peroxymaleic acid, t-butyl peroxybenzoate, acetyl cyclohexyl sulfonyl peroxide and the like; the various azo compounds such as 2-t-butylazo-2-cyanopropane, dimethyl azodiisobutyrate, azodiisobutylronitrile, 2-t-butylazo-1-cyanocyclohexane, 1-t-amylazo-1-cyanocyclohexane and the like, the various alkyl perketals, such as 2,2-bis-(t-butyl-peroxy)butane and the like. Water-soluble peroxygen-free radical initiators are especially useful in such aqueous polymerizations.

The emulsion polymerization is typically carried out at the temperature ranging between about 125° F. (52° C.) and 190° F. (88° C.). At temperatures above about 190° F. (88° C.), alkyl acrylate monomers, such as butyl acrylate, have a tendency to boil. Thus, a pressurized jacket would be required for heating such alkyl acrylate monomers to temperatures in excess of about 88° C. On the other hand, the polymerization reaction proceeds at a very slow rate at temperatures below about 125° F. (52° C.). The slow rate of polymerization experienced at temperatures below about 125° F. (52° C.) results in the polymer having a nonuniform distribution of repeat units in its backbone. The slow rates of polymerization experienced at such low temperatures are also undesirable because they greatly reduce the throughput of the polymerization reactor.

It is generally preferred for the polymerization temperature to be maintained within the range of about 150° F. (66° C.) to 180° F. (82° C.). It is generally more preferred for the reaction temperature to be controlled within the range of about 160° F. (71° C.) to about 170° F. (77° C.). It is important for the polymerization to be conducted at a pH that is below about 3.5 so that a water-sensitive polymer is not produced. It is preferred for the pH of the polymerization medium to be maintained at a level of about 3.0 or less throughout the polymerization. As the polymerization proceeds, the pH of the polymerization medium will drop naturally. Thus, good results can be attained by adjusting the pH of the initial monomer charge composition to within the range of about 3.0 to about 3.5 and allowing the polymerization to proceed. In such a case, the final pH of the polymerization medium will be about 1.5 which is highly satisfactory.

In commercial operations, it is typically desirable to add about 15 percent to about 25 percent of the monomers in an initial charge. The initial charge is then allowed to react for a period of about 30 minutes to about 60 minutes. Then the balance of the monomers to be charged can be continuously charged into the reaction zone at a rate which is sufficient to maintain a reaction temperature within the desired temperature range. By continuously adding the monomers to the reaction medium while maintaining a relatively constant reaction temperature, very uniform polymers can be prepared.

In accordance with the process of this invention, the latex synthesized is then neutralized with ammonia to a pH within the range of about 7 to about 10.5. It is normally preferred for the latex to be neutralized to a pH within the range of 8 to 10 and more preferred for the latex to be neutralized to a pH within the range of about 9.0 to about 9.5. This can be accomplished by simply dispersing ammonia throughout the latex to produce neutralized latex. The ammonia will normally be in the form of ammonium hydroxide.

The latex formed can be diluted with additional water to the concentration (solids content) that is desired. This latex can be used in the preparation of water-reducible coatings using techniques well-known to those skilled in the art. Generally, various pigments and plasticizers are added to the latex in the preparation of the water-reducible coating. Poor adhesion is a problem that is sometimes encountered with water-reducible resins. The adhesion of coatings made with water-reducible resins to substrates can be greatly improved by the addition of a plasticizer.

A film-forming, water-reducible composition, such as a paint, can be prepared by mixing the latex, one or more pigments and a plasticizer. It is not necessary to include a coalescing solvent in the film-forming, water-reducible formulation. For environmental reasons, it is preferred not to include a coalescing solvent in the formulation. However, a small amount (0 to about 50 grams per liter) of coalescing solvent can be included. In cases where a coalescing solvent is employed, it is preferable for it to be at least water-miscible and even more preferable for it to be water-soluble. Of the various coalescing solvents generally ester-alcohols, such as 2,2,4-trimethyl-1,3-pentanediol monoisobutyrate, are preferred.

It should be noted that the pigment, plasticizer and optionally the coalescing solvent can be mixed directly with the resin in its water emulsion or latex. In such an operation, the composite would automatically be in a water-reduced form when sufficient ammonia is used.

Paint formulations can be made utilizing the latices of this invention. Such paint formulations are comprised of one or more pigments and the latex (water, emulsifier system and resin). Such paints can optionally contain fillers, plasticizers, stabilizers, defoamers, dryers, fungicides, insecticides, antifouling agents and anticorrosive agents.

Pigments are normally added to paint formulations to impart color and hiding power to the coating. Titanium dioxide is an example of a widely-used pigment which imparts hiding power and a white color. Mineral pigments, such as oxides of iron and chromium, organic pigments, such as phthalocyanine, and active anticorrosive pigments, such as zinc phosphate, are representative examples of other widely-used pigments.

Fillers are normally inexpensive materials which are added to the paint formulation to attain the desired consistency and non-settling characteristics. Fillers can also improve the physical properties of coatings, such as resistance to cracking and abrasion. Some representative examples of widely utilized fillers include chalks, clays, micas, forms of barites and talcs, and silica.

Driers are chemical compounds, such as salts of cobalt, lead, manganese, barium and zinc, which speed up drying. Stabilizers are chemical agents which neutralize the destructive effects of heat and ultraviolet light. Fungicides and insecticides are commonly added to interior and exterior house paints. Antifouling compounds are commonly added to marine paints to inhibit marine growth. Plasticizers are agents which control the hardness of the film or which impart flexibility.

Of the various plasticizers, it is desired that one be selected which is liquid at room temperature such as 25° C. and have a sufficiently high boiling point, preferably at least 100° C., and even more preferably, at least 150° C., so that they do not volatilize from the coating composition when applied to a substrate. Plasticizers which contain multiple hydroxyl groups should be avoided because their use can lead to instability. The plasticizer should enhance the water insolubility of a dried coating of the coalesced resin. Further, the plasticizer, or mixture of plasticizers, must be characterized by being compatible with the resin itself. For this characterization, a solubility parameter in the range of about 8 to about 16 is required. Such solubility parameter is of the type described in The Encyclopedia of Polymer Science and Technology, Volume 3, Page 854, 1965, John Wiley and Sons, Inc., which is simply determined by the equation $\sigma = (\Sigma F)/V = F/MW/d$ where $\sigma$=solubility parameter
F=sum of the pertinent molar attraction constants of groups determined by Small, P A [(J Appl Chem 3, 71, (1953)]
V=Molar volume at 25° C.
MW=molecular weight
d=density at 25° C.

Various plasticizers can be used for this purpose. They can, for example, be of the type listed in the Federation Series on Coatings Technology, Unit Twenty-two, entitled "Plasticizers," published April 1974, so long as they fulfill the melting point, boiling point and compatibility requirements. Some representative examples of preferred plasticizers include: butyl benzyl phthalate, blends of diethyleneglycol dibenzoate and dipropylene glycol dibenzoate, and 2,2,4-trimethyl-1,3-pentanediol diisobutyrate.

Representative of various plasticizers are cyclic plasticizers such as phosphoric acid esters, phthalic anhydride esters and trimellitic acid esters as well as N-cyclohexyl-p-toluene sulfonamide, dibenzyl sebacate, diethylene glycol dibenzoate, di-t-octylphenylether, dipropane diol dibenzoate, N-ethyl-p-toluene sulfonamide, isopropylidenediphenoxypropanol, alkylated naphthalene, polyethylene glycol dibenzoate, o-p-toluene sulfonamide, trimethylpentanediol dibenzoate and trimethylpentanediol monoisobutyrate monobenzoate.

Representative of various acyclic plasticizers are adipic acid esters, azelaic acid esters, citric acid esters, acetylcitric acid esters, myristic acid esters, phosphoric acid esters, ricinoleic acid esters, acetylricinoleic acid esters, sebacic acid esters, stearic acid esters, epoxidized esters, as well as 1,4-butane diol dicaprylate, butoxyethyl pelargonate di[(butoxyethoxy)ethoxy]methane, dibutyl tartrate, diethylene glycol dipelargonate, diisooctyl diglycolate, isodecyl nonanoate, tetraethylene glycol di(2-ethylbutyrate), triethylene glycol di(2-ethyl-hexanoate), triethylene glycol dipelargonate and 2,2,4-trimethyl-1,3-pentane diol diisobutyrate.

Additional various plasticizers, cyclic, acyclic, and otherwise, include chlorinated paraffins, hydrogenated terphenyls, substituted phenols, propylene glycols, polypropylene glycol esters, polyethylene glycol esters, melamines, epoxidized soys, oils, melamines, liquid, hydrogenated abietate esters, epoxytallate esters, alkyl phthalyl alkyl glycolates, sulfonamides, sebacate esters, aromatic epoxies, aliphatic epoxies, liquid poly($\alpha$-methyl styrene), maleate esters, mellitate esters, benzoates, benzyl esters, tartrates, succinates, isophthalates, orthophthalates, butyrates, fumarates, glutarates, dicaprylates, dibenzoates and dibenzyl esters. It is to be appreciated that relatively low molecular weight polymers and copolymers derived from monoolefins containing 4 to 6 carbon atoms, mixtures of diolefins and monoolefins containing 4 to 6 carbon atoms as well as such hydrocarbons and hydrocarbon mixtures with styrene and/or $\alpha$-methyl styrene can also be used.

The preferred esters are prepared from the reaction of carboxylic and dicarboxylic acids including fatty acids, such as the phthalic acids, benzoic acid, dibenzoic acid, adipic acid, sebacic acid, stearic acid, maleic acid, tartaric acid, succinic acid, butyric acid, fumaric acid and glutaric acid with hydrocarbon diols, preferably saturated hydrocarbon diols, having about 7 to 13 carbon atoms.

Representative of various phosphoric acid esters are cresyl diphenyl phosphate, tricresyl phosphate, dibutyl phenyl phosphate, diphenyl octyl phosphate, methyl diphenyl phosphate, tributyl phosphate, triphenyl phosphate, tri(2-butoxyethyl) phosphate, tri(2-chloroethyl) phosphate, tri-2(chloropropyl) phosphate and trioctyl phosphate.

Representative of various phthalic anhydride esters are butyl octyl phthalate, butyl 2-ethylhexyl phthalate, butyl n-octyl phthalate, dibutyl phthalate, diethyl phthalate, diisodecyl phthalate, dimethyl phthalate dioctyl phthalates, di(2-ethylhexyl)phthalate, diisooctyl phthalate, di-tridecyl phthalate, n-hexyl n-decyl phthalate, n-octyl n-decyl phthalate, alkyl benzyl phthalate, bis(4-methyl-1,2-pentyl)phthalate, butyl benzyl phthalate, butyl cyclohexyl phthalate, di(2-butoxyethyl)phthalate, dicyclohexyl isodecyl phthalate, dicyclohexyl phthalate, diethyl isophthalate, di n-heptyl phthalate, dihexyl phthalate, diisononyl phthalate, di(2-methoxyethyl)phthalate, dimethyl isophthalate, dinonyl phthalate, dioctyl phthalates, dicapryl phthalate, di(2-ethylhexyl)isophthalate, mixed dioctyl phthalates, diphenyl phthalate, 2-(ethylhexyl)isobutyl phthalate, butyl phthalyl butyl glycolate, ethyl (and methyl) phthalyl ethyl glycolate, polypropylene glycol bis(amyl)phthalate, hexyl isodecyl phthalate, isodecyl tridecyl phthalate and isooctyl isodecyl phthalate.

Representative of trimellitic acid esters are triisooctyl trimellitate, tri-n-octyl n-decyl trimellitate, trioctyl trimellitate, tri(2-ethylhexyl)trimellitate, tri-n-hexyl n-decyl trimellitate, tri-n-hexyl trimellitate, triisodecyl trimellitate and triisononyl trimellitate.

Representative of various adipic acid esters are di[2-(2-butoxyethoxy)ethyl]adipate, di(2-ethylhexyl)adipate, diisodecyl adipate, dioctyl adipates (including diisooctyl adipate) n-hexyl n-decyl adipate, n-octyl n-decyl adipate and di-n-heptyl adipate.

Representative examples of sebacic acid esters are dibutyl sebacate, di(2-ethylhexyl)sebacate, dibutoxyethyl sebacate, diisooctyl sebacate and diisopropyl sebacate.

Representative examples of azelaic acid esters are di(2-ethylhexyl)acelate dicyclohexyl acelate, diisobutyl azelate and diisooctyl azelate. In the practice of this invention, the water-reducible composition of resin, plasticizer and coalescing solvent, if used, is water-reduced by neutralizing the carboxyl groups of the resin with ammonia and mixing with water. The resulting dispersion or solution can generally be characterized by being stable without appreciable, if any, precipitation of the resin for a period of at least thirty (30) days and preferably for a period of at least 365 days or more at about 25° C.

Generally, for the purpose of this invention, about 100 to about 400 parts by weight water are used per 100 parts by weight neutralized resin, although more or less water can usually be used depending on whether a high or low viscosity dispersion or solution is desired or whether a high or low solids content is desired. It also depends on the type and amount of coalescing solvent (if any) and plasticizer used. The water-reduced coating composition, as an aqueous dispersion or solution, is applied as a coating onto a suitable substrate such as wood, masonry, various plastics and various metals. The water, ammonia and coalescing solvent are evaporated from the coating, usually at a temperature in the range of about 20° C. to about 100° C., preferably about 25° C. to about 50° C. to leave a substantially water-insoluble coating of the coalesced resin and plasticizer. Generally, such a coating can be prepared and applied without the need for additional hardening agents or curatives to decrease the water sensitivity.

Therefore, it is an important feature of this invention that a durable crosslinked coating is formed on a substrate through the preparation of a particular resin having balanced hydrophilic and hydrophobic elements, preferably with a further balance of hard and soft segments, and the formation of a water-reduced composition of such resin with a combination of pigment and compatible plasticizer. The crosslinking occurs rapidly at ambient temperatures without the need for adding separate curatives or crosslinking agents. Improved adhesion to metal and glass substrates is also attained.

This invention is illustrated by the following examples that are merely for the purpose of illustration and are not to be regarded as limiting the scope of the invention or the manner in which it can be practiced. Unless specifically indicated otherwise, parts and percentages are given by weight.

EXAMPLE 1

General. All reagents were purchased from Gelest unless otherwise noted and used without further purification. Tetrahydropyran-2-ol was prepared according to the literature by the acid catalyzed hydrolysis of dihydropyran (see Bartness J. E.; Hays R. L.; Caldwell G.; *J. Am. Chem. Soc.* 1981, 103, 1338 and March J. in *Advanced Organic Chemistry*, Fourth Ed., Wiley Interscience, N.Y.; p 764). The 0.5 M solution of NaOMe in methanol was purchased from Aldrich.

Experiment 1a. Tetrahydropyran-2-ol (25 g, 0.24 mol) and n-octadecyldimethylmethoxysilane (82 g, 0.24 mol) where reacted with stirring in the presence of a methanol solution of NaOMe (1 g, 0.5 M) for 2 h at 30° C. and reduced pressure (50 Torr). Methanol formed in the reaction and from the NaOMe solution were distilled and the reaction product neutralized with HCl. The n-octadecyldimethylsilane-acetal compound was obtained as a colorless liquid by $^1$H-NMR, $^{13}$C-NMR, $^{29}$Si-NMR.

Experiment 1b. Tetrahydropyran-2-ol (49 g, 0.48 mol) and vinylmethyldiethoxysilane (39 g, 0.24 mol) where reacted with stirring in the presence of a methanol solution of NaOMe (1 g, 0.5 M) for 2 h at 30° C. and reduced pressure (50 Torr). Ethanol formed in the reaction and the methanol from the NaOMe solution were distilled and the reaction product neutralized with HCl. The vinylmethylsilane di-acetal monomer was obtained as a colorless liquid in high purity by $^1$H-NMR, $^{13}$C-NMR, $^{29}$Si-NMR.

Experiment 1c. Tetrahydropyran-2-ol (74 g, 0.72 mol) and 3-methacryloxypropyltrimethoxysilane (60 g, 0.24 mol) where reacted with stirring in the presence of a methanol solution of NaOMe (1 g, 0.5 M) for 2 h at 30° C. and reduced pressure (50 Torr). Methanol formed in the reaction and from the NaOMe solution were distilled and the reaction product neutralized with HCl. The 3-methacryloxypropylsilane tri-acetal monomer was obtained as a colorless liquid in high purity by $^1$H-NMR, $^{13}$C-NMR, $^{29}$Si-NMR.

Experiment 1d. Tetrahydropyran-2-ol (98 g, 0.96 mol) and tetraethylorthosilicate (50 g, 0.24 mol) where reacted with stirring in the presence of a methanol solution of NaOMe (1 g, 0.5 M) for 2 h at 30° C. and reduced pressure (50 Torr). Ethanol formed in the reaction and the methanol from the NaOMe solution were distilled and the reaction product neutralized with HCl. The silane tetra-acetal compound was obtained as a colorless liquid in high purity by $^1$H-NMR, $^{13}$C-NMR, $^{29}$Si-NMR.

EXAMPLE 2

General. The sodium lauryl sulfate was purchased from Proctor and Gamble. The styrene was purchased from Sterling Chemical. The butyl acrylate and ammonium hydroxide were purchased from Aldrich. The methacrylic acid was purchased from Du Pont. The potassium persulfate and ammonium persulfate were purchased from FMC. All materials were used as received without further purification.

Polymerization Procedure. To a 1 gal glass bowl reactor that has been evacuate to less than 25 in Hg for 30 min add the Buffer Solution and the Stage 1 Monomers. Heat to 170° F. and add the Activator Solution. Check the reactor solids after 30 min. If the solids are over 18 wt % add ammonium hydroxide to yield a pH of 9.0. Remove a sample and determine its pH. If the pH is below 9.0 add additional ammonium hydroxide. If solids are below 19 wt % continue the polymerization for an additional 30 min and recheck the polymer solids. The polymerization will overheat to 190° F.–200° F. (88° C.–93° C.). If overheating occurs adjust the reactor temperature to 170° F. (77° C.) and begin adding the Stage 2 Monomers. Adjust the flow rate so that the monomer is added over a period of 2.5 hours. Continue the polymerization at 170° F. (77° C.) until the residual styrene level drops below 500 ppm. If the residual styrene remains above 500 ppm, add 0.1 parts of ammonium persulfate in 200 ml of water and continue the polymerization until the residual styrene is below 500 ppm. Allow the latex to cool before removing it from the reactor. Note that agitation should consist of 2 AFT's rotating 200 rpm.

MEK Rub Testing Procedure. The latex material obtained in the polymerizations was applied by brush on a block on non-porous masonry and allowed to cure at room temperature for 12 h. The resulting film was subjected to methyl ethyl ketone (MEK) rub testing.

Experiment 2a.
  Recipe:
  Buffer Solution
    RO Water: 1472.59 g
    Sodium Lauryl Sulfate (28% active): 3.35 g
  Stage 1 Monomers
    Styrene: 126.88 g
    Butyl Acrylate: 235.63 g
    Methacrylic Acid: 37.50 g
  Activator Solution
    Water: 125 g
    Potassium Persulfate: 3.13 g
  Stage 2 Monomers
    Styrene: 297.50 g
    Butyl Acrylate: 552.50 g Data/Results:
  Solids: 41.6 wt %
  pH: 8.40
  Brookfield Viscosity: 20
  MEK Rub Test (Reciprocations): 3

Experiment 2b.
  Recipe:
  Buffer Solution
    RO Water: 1472.59 g
    Sodium Lauryl Sulfate (28% active): 3.35 g
  Stage 1 Monomers
    Styrene: 126.88 g Butyl Acrylate: 235.63 g
Methacrylic Acid: 37.50 g
Activator Solution
  Water: 125 g
  Potassium Persulfate: 3.13 g
Stage 2 Monomers
  Styrene: 293.75 g
  Butyl Acrylate: 531.25 g
  The 3-methacryloxypropylsilane tri-acetal monomer from Experiment 1c: 25.0 g Data/Results:
  Solids: 41.6 wt %
  pH: 8.44
  Brookfield Viscosity: 25
  MEK Rub Test (Reciprocations): 35

EXAMPLE 3

General. All reagents were purchased from Alrich unless otherwise noted and used without further purification. Tetrahydropyran-2-ol was prepared according to the literature by the acid catalyzed hydrolysis of dihydropyran (see Bartness J. E.; Hays R. L.; Caldwell G.; *J. Am. Chem. Soc.* 1981, 103, 1338 and March J. in *Advanced Organic Chemistry*, Fourth Ed., Wiley Interscience, N.Y.; p 764). All procedures were conducted under nitrogen or in an inert atmosphere dry box using standard Schlenck techniques.

Experiment 3a. A solution of tetrahydropyran-2-ol (21 g, 0.21 mol) in anhydrous diethyl ether (100 mL) was added dropwise to a slurry of NaH (4.7 g, 0.20 mol) in anhydrous diethyl ether (100 mL) with stirring at ca. 25° C. over a period of 2 hours. The resulting white precipitate was filtered and washed with anhydrous diethyl ether (60 mL), collected, and placed under vacuum until reaching a constant weight. The sodium salt of tetrahydropyran-2-ol (NaO-THP) was obtained as a white solid in 86% yield and characterized by $^1$H-NMR and $^{13}$C-NMR.

Experiment 3b. A solution of SiCl$_4$ (3.4 g, 0.02 mol) in anhydrous diethyl ether (75 mL) was added dropwise to a slurry of NaO-THP (10 g, 0.081 mol) in anhydrous diethyl ether (75 mL) with stirring at −78° C. over a period of 2 hours. The resulting heterogeneous mixture was filtered. The filtrate was collected and placed under vacuum until reaching a constant weight. The silane tetra-acetal compound was obtained as a colorless liquid and characterized by $^1$H-NMR, $^{13}$C-NMR, and $^{29}$Si-NMR.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

EXAMPLE 4

Experiment 4a (Polybutylacrylate)

Polybutylacrylate was prepared by emulsion polymerization in a 8 oz glass bottle sealed with a screw cap which contained a rubber gasket and a Teflon liner. The soap solution for the polymerization was prepared from 4.3 g dodecylbenzene sulfonic acid neutralized with ammonium hydroxide in 150 g water treated by reverse osmosis. The soap solution was charged to the bottle followed by 36 g of butylacrylate. Following the charging of the bottle, the head space was purged with nitrogen. The bottles were placed in a polymerization bath controlled at a temperature of 25° C. The bottle was allowed to rotate end-over-end for 30 minutes to disperse the butylacrylate. After 30 minutes, 2 mls of an activator solution containing 22 g of reverse osmosis water, 0.088 g ferric sodium EDTA, and 0.194 g sodium formaldehyde sulfoxylate was charged to the bottle through syringe and the bottle rotated. After 10 minutes, 0.219 g of pinane hydroperoxide was charged to the bottle by syringe to initiate the polymerization and allowed to rotate for 16 hours.

Experiment 4b
Polybutylacrylate-co-Methacryloxypropyl Trimethoxysilane)~10 mole %

The same procedure employed as in Comparative Experiment 4a with the only change being that 30.2 g butylacrylate and 5.9 g methacryloxypropyl trimethoxysilane (A-174) were charged as the monomer solution.

Experiment 4c
(Polybutylacrylate-co-Methacryloxypropyl Trimethoxysilane)~5 mole %

The same procedure employed as in Comparative Experiment 4a with the only change being that 32.8 g butylacrylate and 3.2 g methacryloxypropyl trimethoxysilane (A-174) were charged as the monomer solution.

Experiment 4d
(Polybutylacrylate-co-Methacryloxypropyl Trimethoxysilane)~2.5 mole %

The same-procedure employed as in Comparative Experiment 4a with the only change being that 34.3 g butylacrylate and 1.7 g methacryloxypropyl trimethoxysilane (A-174) were charged as the monomer solution.

Experiment 4e (Polybutylacrylate-co-Modified silane monomer)~10 mole %

The same procedure employed as in Comparative Experiment 4a with the only change being that 26.5 g butylacrylate and 9.5 g of the following monomer were charged as the monomer solution.

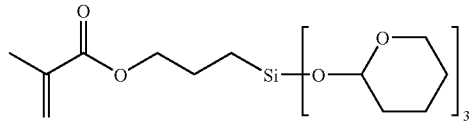

Experiment 4f (Polybutylacrylate-co-protected A174)~5 mole %

The same procedure employed as in Comparative Experiment 4a with the only change being that 30.5 g butylacrylate and 5.5 g of the modified silane containing monomer above were charged as the monomer solution.

Experiment 4g (Polybutylacrylate-co-protected A174)~2.5 mole %

The same procedure employed as in Comparative Experiment 4a with the only change being that 33.05 g butylacrylate and 3.0 g of the modified silane containing monomer above were charged as the monomer solution.

Swelling Test

Latexes were cast on Teflon sheets and allowed to dry at room temperature for three days. Approximately 5 gms of the dried film was placed in 50 mls of toluene and allowed to reach an equilibrium weight. The ratio of the swollen weight to the initial weight was taken as a percentage to determine the degree of swelling of the films.

Aging test

The latex was aged by allowing to stand in a sealed bottle in an oven controlled at 50° C. for thirty days without agitation.

Polymerization Results

| | wt % n-BA | wt % Silane | Mole % Silane | % Conversion |
|---|---|---|---|---|
| Experiment 4a | 100 | 0 | 0 | 100 |
| Experiment 4b | 83.77 | 16.23 | 9.23 | 97.0 |
| Experiment 4c | 91.17 | 8.83 | 4.83 | 98.0 |
| Experiment 4d | 95.39 | 4.61 | 2.55 | 98.9 |
| Experiment 4e | 73.65 | 26.35 | 9.21 | 87.6 |
| Experiment 4f | 84.83 | 15.17 | 4.80 | 92.2 |
| Experiment 4g | 91.81 | 8.19 | 2.32 | 94.1 |

As shown in the table, the conversion of the polymerizations employing the modified silane monomers were less (87%–94%) than the comparative examples (97%–100%).

Swelling Results

| | Mole % Silane | Swelling wt % gain |
|---|---|---|
| Experiment 4a | 0 | Dissolved |
| Experiment 4b | 9.23 | 130 |
| Experiment 4c | 4.83 | 156 |
| Experiment 4d | 2.55 | 278 |
| Experiment 4e | 9.21 | 236 |
| Experiment 4f | 4.80 | 259 |
| Experiment 4g | 2.32 | 393 |

As expected, the degree of swelling decreases as the content of the silane monomers (A174, modified silane-containing monomer) decreases. It is expected that the difference in the degree of swelling at similar silane monomer loading levels is due to incomplete incorporation of the modified silane containing monomer.

Aging Results

| | Mole % Silane | Swelling Time | Swelling % wt gainConversion |
|---|---|---|---|
| Experiment 4b | 9.23 | 0 days | 130 |
| | | 15 days | 276 |
| | | 30 days | 238 |
| Experiment 4e | 9.21 | 0 Days | 226 |
| | | 15 days | 184 |
| | | 30 days | 145 |

The aging results demonstrate the inability of the A-174 monomer to remain stable in an aqueous environment for prolonged periods of time. Initially, the degree of swelling increases indicating the loss of functionality for crosslinking, likely by intra-particle crosslinking. At 30 days, the extent of crosslinking within the bottle is significant enough that the degree of swelling measurement is very dependent upon the ability of the latex to form a cohesive film.

EXAMPLE 5

Adhesive Experimental

General. The following procedure was used to prepare the test samples. The following modified silane reticulating agent was predispersed in a mixture of Igepal CO-880 and 10 wt % NH$_4$OH:

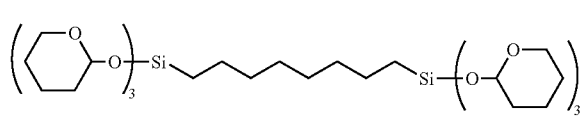

Robond PS-94 was then added and the resulting mixture coated onto a 2 mL polyester sheet using a 40 Mayer Rod. The coated sheets were then dried at 150° F. for 8 minutes. Igepal CO-880 was purchased from GAF Corporation. Robond PS-94 was obtained from Rohm and Haas Company.

| Test Sample | Reticulating Agent | Igepal CO-880 | 10% NH$_4$OH | Robond PS-94 |
|---|---|---|---|---|
| 1 | 0 g | 0.12 g | 3 g | 50 g |
| 2 | 0.66 g | 0.12 g | 3 g | 50 g |
| 3 | 1.3 | 0.24 | 6 g | 50 g |

All experiments were conducted under standard laboratory conditions as set forth in ASTM D3924. The Probe Tack test was conducted according to ASTM D2979. The Peel Adhesion test was performed using stainless steel and was conducted according to PSTC-1. The Shear Adhesion Failure Temperature test was performed using stainless steel and was conducted according to PSTC Appendage B. The modified silane reticulating agent was prepared using the same procedure as Example 3, Experiment 3b with the following changes. A solution of bis(trichlorosilyl)octane (23.25 g, 0.061 mol) in anhydrous diethyl ether (200 mL) was added dropwise to a slurry of NaO-THP (50.49 g, 0.3661 mol) in anhydrous diethyl ether (200 mL) with stirring at −78° C. over a period of 2 hours. The resulting heterogeneous mixture was filtered. The filtrate was collected and placed under vacuum until reaching a constant weight. The modified silane reticulating agent was obtained as a vicous liquid and characterized by $^1$H-NMR, $^{13}$C-NMR, and $^{29}$Si-NMR.

Results.

Probe Tack:

| Test Sample | Polyken Probe Tack (grams) | | | | | | Ave | S Deviation |
|---|---|---|---|---|---|---|---|---|
| | 1 | 2 | 3 | 4 | 5 | 6 | | |
| 1 | 657 | 617 | 624 | 676 | 634 | 599 | 635 | 27.9 |
| 2 | 567 | 564 | 529 | 589 | 575 | 600 | 571 | 24.5 |
| 3 | 547 | 487 | 509 | 516 | 479 | 451 | 498 | 33.3 |

These test results show that the modified silane reticulating agent reduces tack in increasing amount, thus demonstrating increased cure and crosslinking over the control sample which did not contain the modified silane reticulating agent.

Experiment Peel Adhesion:

| Test Sample | PSTC-1 Peel Adhesion (lbs/inch width) | | | | |
|---|---|---|---|---|---|
| | 1 | 2 | 3 | Average | S Deviation |
| 1 | 1.69 | 1.54 | 1.50 | 1.58 | 0.10 |
| 2 | 1.84 | 1.85 | 1.88 | 1.86 | 0.02 |
| 3 | 1.99 | 1.85 | 1.87 | 1.90 | 0.08 |

These test results show that the modified silane reticulating agent increases adhesion, in increasing amount compared to the control sample which did not contain the modified silane reticulating agent.

Shear adhesion Failure Temperature:

| Test Sample | Shear Adhesion Failure Temperature (deg F.) | | | |
|---|---|---|---|---|
| | 1 | 2 | Average | S Deviation |
| 1 | 267.0 | 266.0 | 266.5 | 0.7 |
| 2 | >400 | >400 | >400 | 0.0 |
| 3 | 259.0 | 261.0 | 260.0 | 1.4 |

These test results show that the modified silane reticulating agent increases the temperature at which adhesion failure occurs and further shows that this property is only improved at lower levels of the modified reticulating agent.

What is claimed is:

1. A monomer having a structural formula selected from the group consisting of:

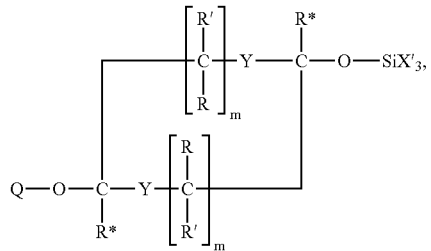
(1)

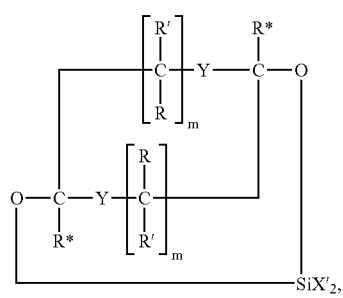
(2)

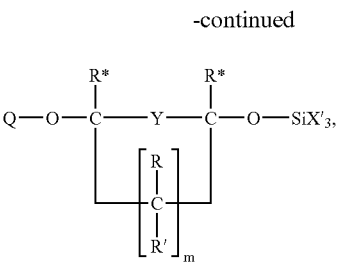
(3)

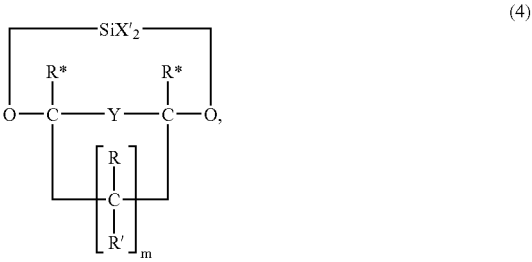
(4)

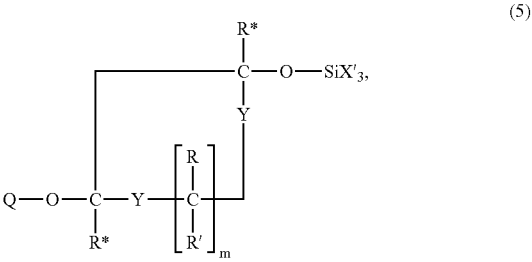
(5)

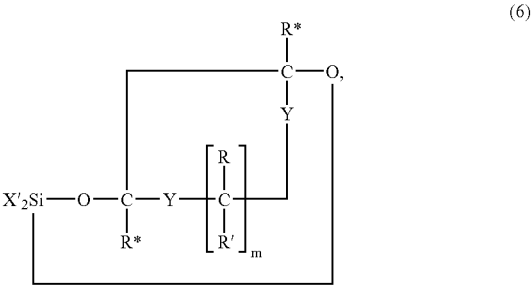
(6)

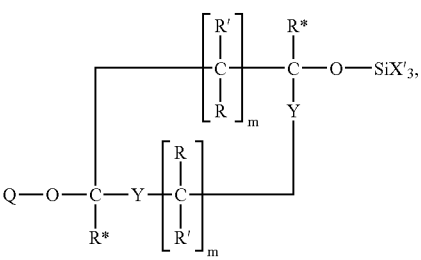
(7)

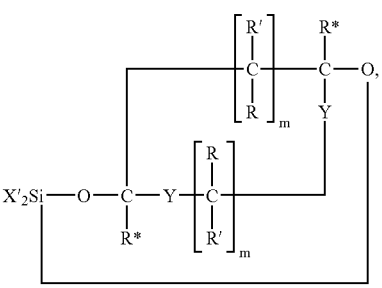
(8)

-continued (9)

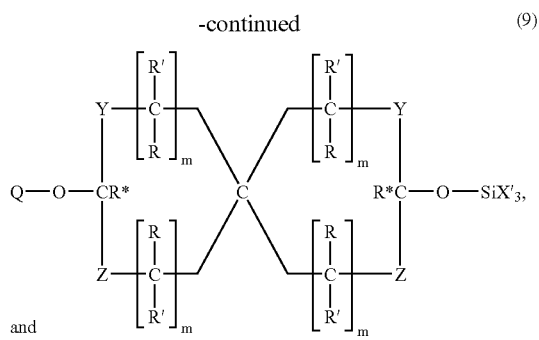

and (10)

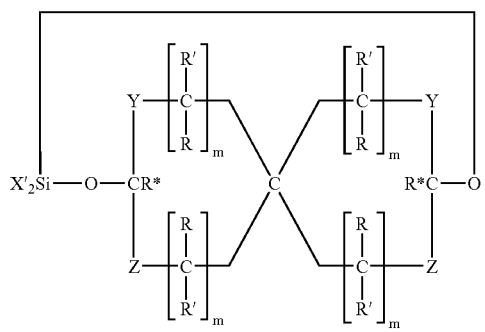

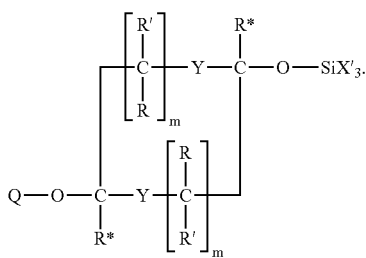

3. A monomer as specified in claim 1 wherein the monomer is of the structural formula:

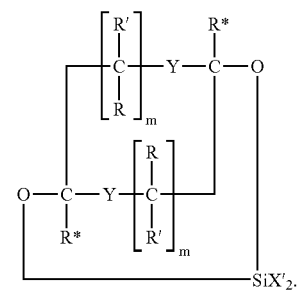

wherein m represents an integer from 1 to about 20; wherein X' groups can be the same or different; wherein X' represents an unsaturated moiety containing at least one non-aromatic double bond; wherein Q is selected from the group consisting of hydrogen atoms and SiX'$_3$; wherein R and R' can be the same or different and are selected from the group consisting of hydrogen atoms, alkyl groups containing from 1 to about 12 carbon atoms, aryl groups containing from about 6 to about 18 carbon atoms, alkaryl groups containing from 7 to about 18 carbon atoms, alkoxy groups containing from 1 to about 18 carbon atoms, hydroxy groups, and halide atoms; wherein R* is selected from the group consisting of hydrogen atoms, alkyl groups containing from 1 to about 12 carbon atoms, aryl groups containing from about 6 to about 18 carbon atoms, and alkaryl groups containing from 7 to about 18 carbon atoms; wherein R, R', and R* can be bonded together in any combination in cases where R, R', and R* are not hydrogen atoms, halide atoms, or hydroxy groups; wherein Y represents a moiety selected from the group consisting of oxygen, sulfur, nitrogen, and phosphorus; wherein Z represents a moiety selected from the group consisting of C(R)R', oxygen, sulfur, nitrogen, and phosphorus; wherein the contiguous cyclic ring in formulas (1), (2), (3), (4), (5), (6), (7), (8), (9), and (10) can contain heteroatoms selected from the group consisting of oxygen, sulfur, nitrogen, phosphorus, and silicon in cases where m represents an integer greater than 1; wherein the contiguous cyclic ring in formulas (1), (2), (3), (4), (5), (6), (7), (8), (9), and (10) can be saturated or unsaturated in cases where m represents an integer greater than 1; wherein said alkyl groups, aryl groups, alkaryl groups, and alkoxy groups can contain halide atoms and heteroatoms selected from the group consisting of oxygen, sulfur, nitrogen, phosphorus, and silicon.

2. A monomer as specified in claim 1 wherein the monomer is of the structural formula:

4. A monomer as specified in claim 1 wherein the monomer is of the structural formula:

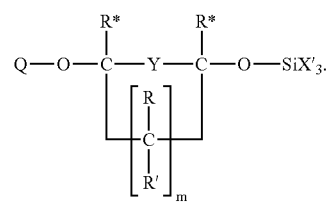

5. A monomer as specified in claim 1 wherein the monomer is of the structural formula:

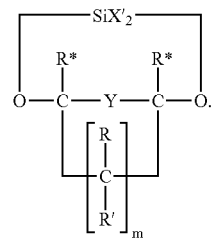

6. A monomer as specified in claim 1 wherein the monomer is of the structural formula:

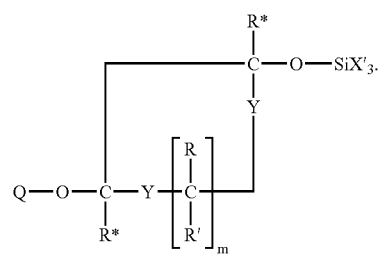

7. A monomer as specified in claim 1 wherein the monomer is of the structural formula:

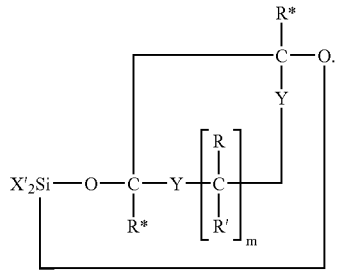

8. A monomer as specified in claim 1 wherein the monomer is of the structural formula:

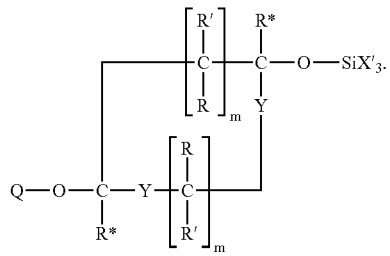

9. A monomer as specified in claim 1 wherein the monomer is of the structural formula:

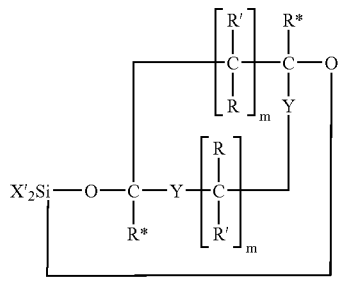

10. A monomer as specified in claim 1 wherein the monomer is of the structural formula:

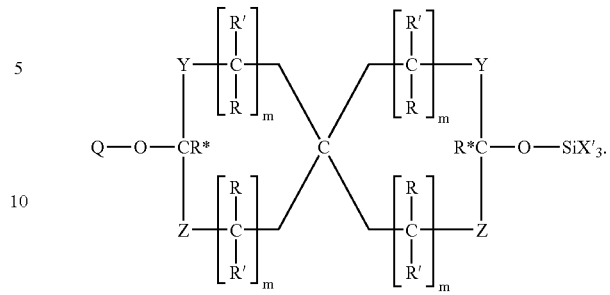

11. A monomer as specified in claim 1 wherein the monomer is of the structural formula:

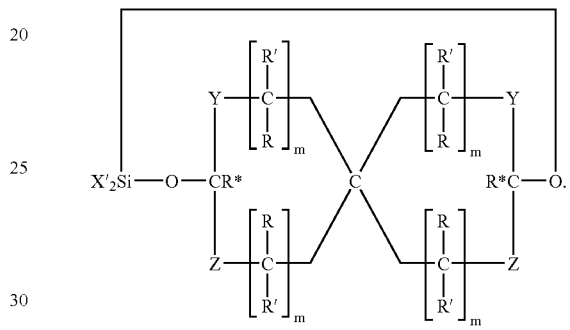

12. A monomer as specified in claim 2 wherein Y is oxygen.
13. A monomer as specified in claim 3 wherein Y is oxygen.
14. A monomer as specified in claim 4 wherein Y is oxygen.
15. A monomer as specified in claim 5 wherein Y is oxygen.
16. A monomer as specified in claim 6 wherein Y is oxygen.
17. A monomer as specified in claim 7 wherein Y is oxygen.
18. A monomer as specified in claim 8 wherein Y is oxygen.
19. A monomer as specified in claim 9 wherein Y is oxygen.
20. A monomer as specified in claim 10 wherein Y is oxygen and Z is C(R)R'.

* * * * *